(12) United States Patent
Kosugi et al.

(10) Patent No.: US 10,772,273 B2
(45) Date of Patent: Sep. 15, 2020

(54) POWDERY MILDEW RESISTANCE MARKER FOR MELON PLANTS, POWDERY MILDEW RESISTANT MELON PLANT, AND METHOD FOR PRODUCING POWDERY MILDEW RESISTANT MELON PLANT USING THE SAME

(71) Applicant: Takii & Company Limited, Kyoto (JP)

(72) Inventors: Kazuo Kosugi, Kyoto (JP); Ryohei Arimoto, Kyoto (JP); Daisuke Maeda, Kyoto (JP); Akihito Kano, Kyoto (JP); Ryuji Ikesue, Kyoto (JP)

(73) Assignee: Takii & Company Limited, Kyoto (JP)

( * ) Notice: Subject to any disclaimer, the term of this patent is extended or adjusted under 35 U.S.C. 154(b) by 59 days.

(21) Appl. No.: 15/775,637

(22) PCT Filed: May 31, 2016

(86) PCT No.: PCT/JP2016/066009
§ 371 (c)(1),
(2) Date: May 11, 2018

(87) PCT Pub. No.: WO2017/081876
PCT Pub. Date: May 18, 2017

(65) Prior Publication Data
US 2018/0325057 A1    Nov. 15, 2018

(30) Foreign Application Priority Data
Nov. 13, 2015  (JP) .................................. 2015-222794

(51) Int. Cl.
| | | |
|---|---|---|
| *A01H 1/02* | (2006.01) | |
| *A01H 1/04* | (2006.01) | |
| *A01H 6/34* | (2018.01) | |
| *A01H 5/08* | (2018.01) | |
| *C12Q 1/6895* | (2018.01) | |

(52) U.S. Cl.
CPC ................. *A01H 1/02* (2013.01); *A01H 1/04* (2013.01); *A01H 5/08* (2013.01); *A01H 6/344* (2018.05); *C12Q 1/6895* (2013.01); *C12Q 2600/13* (2013.01)

(58) Field of Classification Search
None
See application file for complete search history.

(56) References Cited

PUBLICATIONS

Argyris et al., "Use of targeted Snp selection for an improved anchoring of the melon (*Cucumis melo* L) scaffold genome assembly," BMC Genomics, 16: 1-14 (2015).

Beraldo-Hoischen et al., "QTL associated with one recessive gene for powdery mildew resistance in the melon genotype TGR-1551," Cucurbitaceae, 508-513 (2012).

Fukino et al., "Identification of QTLs for resistance to powdery mildew and SSR markers diagnostic for powdery mildew resistance genes in melon (*Cucumis melo* L)," Theoretical and Applied Genetics, 118: 165-175 (2008).

Fazza et al., "Mapping of resistance genes to races 1,3 and 5 of Podosphaera xanthii in melon PI 414723," Crop Breeding and Applied Biotechnology, 13: 349-355 (2013).

Kuzuya et al., "Melon Breeding for Resistance to Powdery Mildew in Respect to Its Races," Proceedings of Vegetable and Tea Science, 39-43 (2004) (see partial translation).

Liu et al., "A Sequence-amplified Characterized Region Marker for a Single, Dominant Gene in Melon PI 134198 that Confers Resistance to a Unique Race of Podosphaera xanthii in China," HortScience, 45: 1407-1410 (2010).

McCreight et al., "Cucurbit powdery mildew of melon incited by Podosphaera xanthii: Global and western U.S. Perspectives," Cucurbitaceae, 181-189 (2012).

McCreight et al., "Inheritance of Resistance in Melon PI 313970 to Cucurbit Powdery Mildew Incited by Podosphaera kanthii Race S," HortScience, 46: 838-840 (2011).

Perchepied et al., "Relationship Between Loci Conferring Downy Mildew and Powdery Mildew Resistance in Melon Assessed by Quantitative Trait Loci Mapping," Phytopathology, 95: 556-565 (2005).

Pitrat, "2006 Gene List for Melon," Cucurbit Genetics Cooperative Report, 28-29: 142-163 (2005-2006).

Pitrat et al., "Inheritance of Podosphaera xanthii resistance in melon line '90625'," Cucurbitaceae, 135-142 (2008).

Sales Junior et al., "Reaction of families and lines of melon to powdery mildew," Horticultura Brasileira, 29: 382-386 (2011).

Takada et al., "Studies on the Breeding of Melon for Resistance to Powdery Mildew, I Difference of Resistance among Varieties and the Breeding of the Resistant Variety 'Sunrise'," Bulletin of the Vegetable and Ornamental Crops Research Station, Series A, 59-91 (1974) (see partial translation).

Yuste-Lisbona et al., "Genetic linkage map of melon (*Cucumis melo* L.) and localization of a major QTL for powdery mildew resistance," Molecular Breeding, 27: 181-192 (2011).

Yuste-Lisbona et al., "Inheritance of resistance to races 1,2 and 5 of powdery mildew in the melon TGR-1551," Plant Breeding, 129: 72-75 (2010).

(Continued)

*Primary Examiner* — Brent T Page
(74) *Attorney, Agent, or Firm* — Morgan, Lewis & Bockius LLP

(57) ABSTRACT

The present disclosure provides a novel powdery mildew resistance marker for melon plants, a powdery mildew resistant melon plant including a powdery mildew resistance locus; and a method for producing a powdery mildew resistant melon plant using the same.

11 Claims, 2 Drawing Sheets
Specification includes a Sequence Listing.

(56) References Cited

PUBLICATIONS

Yuste-Lisbona et al., "Codominant PCR-based markers and candidate genes for powdery mildew resistance in melon (*Cucumis melo* L.)," Theoretical and Applied Genetics, 122: 747-758 (2011).
Zhang et al., "Application of comparative genomics in developing markers tightly linked to the Pm-2F gene for powdery mildew resistance in melon (*Cucumis melo* L.)," Euphytica, 190: 157-168 (2013).
Third Party Observation for the International Patent Application No. PCT/JP2016/066099 dated Mar. 12, 2018.
Melon, Vedrantais, https://www.burpee.com/vegetables/melon/melon-vedrantais-prod002040.html (retrieved May 10, 2018).
International Search Report issued in corresponding International Patent Application No. PCT/JP2016/066009 dated Aug. 16, 2016.
Melonomics Project (website https://www.melonomics.net) (Jul. 3, 2018).
Melonomics Project (website https://melonomics.net) (Jul. 3, 2018).
International Union for the Protection of New Varieties of Plants: Geneva, Technical Working Party for Vegetables, Forty-Seventh Session, Nagasaki, Japan May 20-24, 2013, Partial Revision of the Test Guidelines for Melon.
DNA Data Bank of Japan, Locus LC516691, Cucumis melo SVI 0105 DNA, flanking region of predicted gene required for powdery mildew resistance (No. 3), Jan. 10, 2020.
DNA Data Bank of Japan, Locus LC516692, Cucumis melo SVI 0105 DNA, flanking region of predicted gene required for powdery mildew resistance (No. 4), Jan. 10, 2020.
DNA Data Bank of Japan, Locus LC516693, Cucumis melo SVI 0105 DNA, flanking region of predicted gene required for powdery mildew resistance (No. 5), Jan. 10, 2020.
DNA Data Bank of Japan, Locus LC516694, Cucumis melo SVI 0105 DNA, flanking region of predicted gene required for powdery mildew resistance (No. 3), Jan. 10, 2020.
Alignment diagrams of sequence ID Nos. 3-6 in the present specifications, LC516691.1.
Third Party Submission Reasons for Submission filed in corresponding Japanese Patent Application No. 2015-222794 dated Feb. 20, 2020.

Disease index 0

Disease index 1

Disease index 3

Disease index 4

SEQUENCE LISTING

```
<160> NUMBER OF SEQ ID NOS: 13

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
aatctcaaca agtgagcttt tattgt                                              26

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
catgattatc ttcaattttc tttttgtc                                            28

<210> SEQ ID NO 3
<211> LENGTH: 567
```

<212> TYPE: DNA
<213> ORGANISM: Cucumis melo

<400> SEQUENCE: 3

```
ggaaaaatgc aggggaaggc gaagagcagc cttcggagag gaaaaaaatt tttttggttg      60
aacataacat actattggta gttggaattc caagtatgag cacagattga aaggcattta     120
tttgcaagtc acttcctcat cctcctcgaa gtcttttgct ttcaccctat tgcagattct     180
atgcccactg aaattctctc tgtaaaagct ccatcttcca actcgtcctc tgctgctctt     240
tcttttctt  ctctctcttc cttagccaaa tctaggtcaa aggctaagtc taaaaaacca     300
tccaaaatca aggattctct cacatcctct gggtttcact tgtttgttta attcgtttgt     360
acttttgttt atgattactc ttttcgctct aagtataatt ctcatgtact tgagcatta     420
gtctcttttg ttaatacatt taagaggct cgtatcaatg tttggtgctg acctccaagg     480
aaatatccaa caacttttag ttgaggtgca cttaaaaata tttccctcaa tcactttgga     540
tacatgcggt taagtcgctt ttggcag                                         567
```

<210> SEQ ID NO 4
<211> LENGTH: 497
<212> TYPE: DNA
<213> ORGANISM: Cucumis melo

<400> SEQUENCE: 4

```
aggaaacgaa gaatagacga aatgtcaagg ttgctattct aataccatgc ttcccaagtc      60
agaccagctt cattccagca tatggtatca agagattcta ttgacgtgac ttctaatgtc     120
tcttccacac ctactccaga aattccccaa tttcatttag attaacattt tacagtcgaa     180
tcaatcccac caacccagtc atttataatc tgctaatttc tggactgtgc aacgacaaat     240
cctgcacaga caaggcctac gatagtttgt gcaaccagac tcctgacatg aatatccatt     300
ctcccattat tgctgagatt catctcgtat atacttaatc caacttctta cattgccaaa     360
aaatttctgg cctacaaagc aaatatgacc ctaaacttga agaaaccaat attgtaaaag     420
ctttaactca acatatgagg agatattttt atgccaaaca taatcaagaa aagataagct     480
tctctttccg gttctca                                                   497
```

<210> SEQ ID NO 5
<211> LENGTH: 462
<212> TYPE: DNA
<213> ORGANISM: Cucumis melo

<400> SEQUENCE: 5

```
gttcggatcg gaaaattcaa tcaaaggaat aagcgctaca aaacaataaa cacacacata      60
catccaaaaa ttacaaatct cctatcatca tcaagaaaca gaaaaaccaa accgaaaacg     120
aaataaacgc caaataattt cagaaaatcg atgcgacgga ataagaaatg catgtatctg     180
gtatgatcga aagagaaaat atacgagatc cggtggtttg ccagagctgc atctcgccgt     240
cttcataatc gccttcggga cgaacggcga tgagaacaag gtaatcgccc ttgcggacaa     300
cgttgtcgat ggcccatttg agggcttaa  tgctgcaggc agagaaatcc accgcgacgc     360
cgactctccg ttgaccgtcc atgcttttg  tgggttggga ttttcagtgc gtttgagctt     420
tgtggaagga aggaagaatg gaatgaatgt cggaaagctt gg                       462
```

<210> SEQ ID NO 6
<211> LENGTH: 133
<212> TYPE: DNA

<213> ORGANISM: Cucumis melo

<400> SEQUENCE: 6

```
aatctcaaca agtgagcttt tattgtaaaa aatacaacac aagtaagagt gtgtgtattt    60
ataattgaaa gaagaagaag aagaagaaga agaagaagaa aacaagacaa aaagaaaatt   120
gaagataatc atg                                                      133
```

<210> SEQ ID NO 7
<211> LENGTH: 10
<212> TYPE: DNA
<213> ORGANISM: Cucumis melo

<400> SEQUENCE: 7

```
aaaagctcca                                                           10
```

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8

```
ggaaaaatgc aggggaag                                                  18
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9

```
ctgccaaaag cgacttaacc                                                20
```

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10

```
aggaaacgaa gaatagacg                                                 19
```

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11

```
tgagaaccgg aaagagaagc                                                20
```

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12

```
gttcggatcg gaaaattcaa                                                20
```

```
<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccaagctttc cgacattcat                                           20
```

POWDERY MILDEW RESISTANCE MARKER FOR MELON PLANTS, POWDERY MILDEW RESISTANT MELON PLANT, AND METHOD FOR PRODUCING POWDERY MILDEW RESISTANT MELON PLANT USING THE SAME

SEQUENCE LISTING SUBMISSION VIA EFS-WEB

A computer readable text file, entitled "SequenceListing.txt," created on or about May 10, 2018 with a file size of about 5 kb contains the sequence listing for this application and is hereby incorporated by reference in its entirety.

TECHNICAL FIELD

The present invention relates to a powdery mildew resistance marker for melon plants, a powdery mildew resistant melon plant, and a method for producing a powdery mildew resistant melon plant using the same.

BACKGROUND ART

In cultivation of melon plants, a disease caused by powdery mildew fungus is a serious problem worldwide. Plant bodies infected with the powdery mildew fungus grow poorly owing to withering of leaves, etc. As a result, the yield of fruits is reduced.

Under these circumstances, attempts have been made to breed melon cultivars resistant to the powdery mildew fungus utilizing powdery mildew resistance genes. However, appearance of species of powdery mildew fungi capable of infecting melon plants including these resistance genes gives rise to a problem (Non-Patent Document 1).

CITATION LIST

Non-Patent Document(s)

[Non-Patent Document 1] F. J. Yuste-Lisbona et al., "Inheritance of resistance to races 1, 2 and 5 of powdery mildew in the melon TGR-1551", Plant Breeding, 2010, vol. 129, pp. 72-75

BRIEF SUMMARY OF THE INVENTION

Problem to be Solved by the Invention

With the foregoing in mind, it is an object of the present invention to provide a novel powdery mildew resistance marker for melon plants, a powdery mildew resistant melon plant including a powdery mildew resistance locus, and a method for producing a powdery mildew resistant melon plant using the same.

Means for Solving Problem

In order to achieve the above object, the present invention provides a powdery mildew resistance marker for a melon plant, including: a powdery mildew resistance locus on chromosome 6 in a homozygous form, wherein the powdery mildew resistance locus on chromosome 6 satisfies at least one of the following conditions (1) and (2).
Condition (1):
The powdery mildew resistance locus on chromosome 6 is identified by a length of an amplified fragment obtained by amplification using the following primer set 1, and the length of the amplified fragment is 133 bp or more.
Primer set 1:
a forward primer 1 consisting of a base sequence of SEQ ID NO: 1
a reverse primer 1 consisting of a base sequence of SEQ ID NO: 2
Condition (2):
The powdery mildew resistance locus on chromosome 6 is identified by polymorphisms of bases at positions 45, 48, 49, 51, 108, 120, 139, 214, and 327 in a base sequence of SEQ ID NO: 3.

The present invention also provides a powdery mildew resistant melon plant including: a powdery mildew resistance locus on chromosome 6 in a homozygous form, wherein the powdery mildew resistance locus on chromosome 6 satisfies at least one of the following conditions (1) and (2).
Condition (1):
The powdery mildew resistance locus on chromosome 6 is identified by a length of an amplified fragment obtained by amplification using the following primer set 1, and the length of the amplified fragment is 133 bp or more.
Primer set 1:
a forward primer 1 consisting of a base sequence of SEQ ID NO: 1
a reverse primer 1 consisting of a base sequence of SEQ ID NO: 2
Condition (2):
The powdery mildew resistance locus on chromosome 6 is identified by polymorphisms of bases at positions 45, 48, 49, 51, 108, 120, 139, 214, and 327 in a base sequence of SEQ ID NO: 3.

The present invention also provides a method for producing a powdery mildew resistant melon plant, including the following steps (a) and (b):
(a) crossing the powdery mildew resistant melon plant according to the present invention with another melon plant; and
(b) selecting a powdery mildew resistant melon plant from one or more melon plants obtained in the step (a) or progeny lines thereof.

Effects of the Invention

The inventors of the present invention conducted diligent studies, and discovered a novel powdery mildew resistance locus for melon plants as a powdery mildew resistance marker exhibiting powdery mildew resistance. Melon plants including the powdery mildew resistance marker exhibit powdery mildew resistance. Thus, the powdery mildew resistance marker for melon plants according to the present invention enables easy screening for powdery mildew resistant melon plants, for example. Also, the powdery mildew resistant melon plant according to the present invention includes the powdery mildew resistance locus, and thus can exhibit powdery mildew resistance, for example. Further, the powdery mildew resistance locus can confer the powdery mildew resistance while it is a single gene locus (monogenic factor), for example. Thus, according to the powdery mildew resistant melon plant of the present invention, for example, progenies exhibiting powdery mildew resistance can be obtained easily also from F1 obtained by crossing the powdery mildew resistant melon plant of the present invention with other melon plants or progenies thereof. Furthermore, a melon plant including the powdery mildew resistance marker is resistant to races of powdery mildew fungus capable of infecting melon plants including the powdery mildew resistance genes disclosed in the prior art document, for example. Thus, the powdery mildew resistant melon plant of the present invention can eliminate the necessity of prevention and extermination using agricultural chemicals as performed conventionally, so that the problem of labor and cost for spraying the agricultural chemicals can be avoided, for example.

MODE FOR CARRYING OUT THE INVENTION

Figure 1:
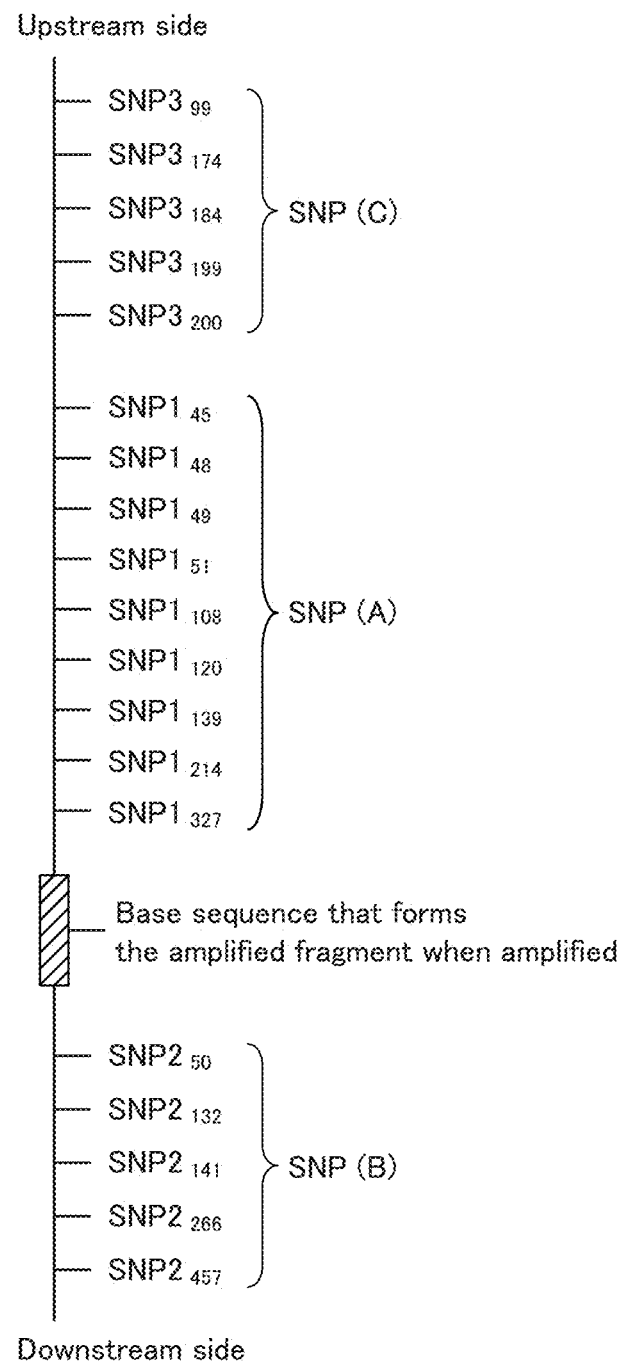
FIG. 1 is a schematic view showing relative locations of single nucleotide polymorphisms (SNPs) and the like on chromosome 6.

1. Powdery Mildew Resistance Marker for Melon Plants

The powdery mildew resistance marker for a melon plant (also referred to simply as "resistance marker" hereinafter) according to the present invention is, as described above, a powdery mildew resistance marker for a melon plant, including: a powdery mildew resistance locus on chromosome 6 in a homozygous form, wherein the powdery mildew resistance locus on chromosome 6 satisfies at least one of the following conditions (1) and (2).
Condition (1):
The powdery mildew resistance locus on chromosome 6 is identified by a length of an amplified fragment obtained by amplification using the following primer set 1, and the length of the amplified fragment is 133 bp or more.
Primer set 1:
 a forward primer 1 consisting of a base sequence of SEQ ID NO: 1
 a reverse primer 1 consisting of a base sequence of SEQ ID NO: 2
Condition (2):
The powdery mildew resistance locus on chromosome 6 is identified by polymorphisms of bases at positions 45, 48, 49, 51, 108, 120, 139, 214, and 327 in a base sequence of SEQ ID NO: 3.

The powdery mildew resistance marker of the present invention is characterized in that it includes a powdery mildew resistance locus on chromosome 6 in a homozygous form and that the powdery mildew resistance locus on chromosome 6 satisfies at least one of the conditions (1) and (2). Other configurations or conditions are not particularly limited.

In the present invention, "melon plants" are plants classified in *Cucumis melo* of the genus *Cucumis*.

In the present invention, examples of the pathogen of powdery mildew include *Sphaerotheca fuliginea* (also referred to as "*Podosphaera xanthii*") and *Erysiphe polygoni*.

In the present invention, the term "powdery mildew resistance" also may be referred to as "powdery mildew tolerance", for example. The resistance means the ability to inhibit or suppress the occurrence and progression of damage due to the infection with the pathogen of powdery mildew, for example. Specifically, the resistance may mean any of the following, for example: to prevent the damage from occurring; to stop the progression of the damage that has occurred already; and to suppress (also referred to as "inhibit") the progression of the damage that has occurred already.

In the present invention, the "chromosome" also can be referred to as "linkage group", for example. Thus, in the present invention, chromosomes 1 to 12 of a melon plant also can be referred to as, for example, linkage groups 1 to 12, respectively, and chromosome 6 also can be referred to as, for example, linkage group 6. The linkage groups can be determined on the basis of genome sequence information on melon plants with reference to the following Reference Document 1, for example. The genome sequence information on melon plants is available on the website (https://melonomics.net/) of MELONOMICS Project, for example. Specifically, chromosome 6 (linkage group 6) in the present invention can be determined on the basis of a piece of genome sequence information, Melon_genome_v3.5.1, on melon plants disclosed on the website of MELONOMICS Project with reference to the following Reference Document 1, for example.

Reference Document 1: Jason M. Argyris et al., "Use of targeted SNP selection for an improved anchoring of the melon (*Cucumis melo* L.) scaffold genome assembly", BMC Genomics, 2015 vol. 16: 4

While the resistance marker of the present invention includes the resistance locus on chromosome 6 in a homozygous form as described above, the powdery mildew resistant melon plant may include the resistance locus on chromosome 6 on, instead of on chromosome 6, any chromosome other than chromosome 6, for example. That is, the powdery mildew resistant melon plant may include the resistance locus on chromosome 6 on any of chromosome 1, chromosome 2, chromosome 3, chromosome 4, chromosome 5, chromosome 7, chromosome 8, chromosome 9, chromosome 10, chromosome 11, and chromosome 12. When the powdery mildew resistant melon plant includes the resistance marker on any chromosome other than chromosome 6, the powdery mildew resistant melon plant may include one resistance locus on a chromosome other than chromosome 6 or two resistance loci on a chromosome(s) other than chromosome 6, for example. In the latter case, the powdery mildew resistant melon plant may include the two resistance loci on the same chromosome or on different chromosomes, for example.

The powdery mildew resistance locus refers to a quantitative trait locus or a gene region that confers the powdery mildew resistance. In general, the quantitative trait locus (QTL) refers to a chromosome region that is involved in the expression of a quantitative trait. The QTL can be specified using a molecular marker that indicates a specific locus on a chromosome. The technique for specifying the QTL using the molecular marker is well known in the art.

In the present invention, a molecular marker used for specifying (also referred to as "identifying" hereinafter) the powdery mildew resistance locus is not particularly limited. Examples of the molecular marker include SNP markers, amplified fragment length polymorphism (AFLP) markers, restriction fragment length polymorphism (RFLP) markers, microsatellite markers, sequence-characterized amplified region (SCAR) markers, and cleaved amplified polymorphic sequence (CAPS) markers. Examples of the microsatellite markers include short tandem repeat (STR) markers and simple sequence repeat (SSR) markers. The resistance locus may be identified by one type of marker or by two or more types of markers, for example.

In the present invention, one SNP marker may be used, or two or more SNP markers may be used in combination, for example.

In the present invention, the resistance locus satisfies: (i) a condition based on at least one of the length of each of the amplified fragments obtained by amplification using the primer set and the combination of polymorphisms (also referred to as "SNPs" hereinafter) of bases. That is, the resistance locus satisfies at least one of the conditions (1) and (2), as described above. Further, the resistance locus may satisfy, for example, (ii) a condition based on at least one of the base sequence of each of the amplified fragments obtained by amplification using the primer set and a base sequence including the combination of SNPs; (iii) a condition based on the base sequence of a region including at least one of the base sequence of each of the amplified fragments obtained by amplification using the primer set and a base sequence including the combination of SNPs; or any combination of (i) to (iii), as will be described below. When the resistance locus satisfies any combination of (i) to (iii), the combination is not particularly limited, and examples thereof include the following combinations. While the resistance locus satisfies (i), the present invention is not limited thereto. For example, instead of (i), the resistance locus may satisfy (ii) or (iii), or may satisfy the combination of (ii) and (iii).
Combination of (i) and (ii)
Combination of (i) and (iii)
Combination of (i), (ii), and (iii)

(i) Condition Based on Length of Amplified Fragment and Combination of SNPs

As described in the above item (i), the resistance locus satisfies the condition based on at least one of the length of each of the amplified fragments obtained by amplification using the primer set and the combination of SNPs, and specifically, the resistance locus satisfies at least one of the conditions (1) and (2). In the following description, SNPs in the respective conditions are newly identified by the inventors of the present invention, and those skilled in the art can identify the chromosomal locations of these SNPs on the basis of the base sequences including these SNPs to be described below.

In the condition (1), the resistance locus is identified by the length of each of the amplified fragments obtained by amplification using the following primer set 1. The length of the amplified fragment can be measured by, for example, amplifying the gene of a melon plant using the following primer set 1 and analyzing the resultant amplified fragment. The analysis of the amplified fragment may be sequencing of the amplified fragment or analysis by electrophoresis or the like, for example. The following primer set 1 amplifies, for example, the base sequence from positions 5857028 to 5857159 on chromosome 6 in the above-described genome sequence information on melon plants.

```
Primer set 1
a forward primer 1:
                                         (SEQ ID NO: 1)
5'-AATCTCAACAAGTGAGCTTTTATTGT-3' a reverse primer 1:
                                         (SEQ ID NO: 2)
5'-CATGATTATCTTCAATTTTCTTTTTGTC-3'
```

The length of the amplified fragment may be 133 bp or more, and the upper limit of the length of the amplified fragment is not particularly limited. The upper limit of the length of the amplified fragment may be, for example, 140 bp or less or 135 bp or less, and the range of the length of the amplified fragment may be, for example, from 133 bp to 140 bp or from 133 bp to 135 bp. Preferably, the length of the amplified fragment is 133 bp. The relevance of the length of the amplified fragment obtained by amplification using the primer set 1 with the powdery mildew resistance has not been reported heretofore. The length of the amplified fragment is a novel length of an amplified fragment discovered first by the inventors of the present invention as being involved in the powdery mildew resistance.

In the condition (2), the resistance locus is identified by the combination of nine types of SNPs (also referred to as "first SNP set" hereinafter) in the base sequence of SEQ ID NO: 3 shown below. The nine types of SNPs are SNPs at positions 45, 48, 49, 51, 108, 120, 139, 214, and 327 in the base sequence of SEQ ID NO: 3. Hereinafter, the SNPs at positions 45, 48, 49, 51, 108, 120, 139, 214, and 327 also are referred to as "SNP1$_{45}$", "SNP1$_{48}$", "SNP1$_{49}$", "SNP1$_{51}$", "SNP1$_{108}$", "SNP1$_{120}$", "SNP1$_{139}$", "SNP1$_{214}$", and "SNP1$_{327}$", respectively. SNP1$_{45}$, SNP1$_{48}$, SNP1$_{49}$, SNP1$_{51}$, SNP1$_{108}$, SNP1$_{120}$, SNP1$_{139}$, SNP1$_{214}$, and SNP1$_{327}$ are the 1st to 9th underlined bases in brackets in the base sequence of SEQ ID NO: 3, respectively. The base sequence of SEQ ID NO: 3 can be obtained from the melon plant deposited under Accession No. FERM BP-22291 to be described below, for example. The base sequence of SEQ ID NO: 3 corresponds to, for example, the base sequence from positions 5586975 to 5587541 on chromosome 6 in the above-described genome sequence information on melon plants.

```
                                              SEQ ID NO: 3
5'-GGAAAAATGCAGGGGAAGGCGAAGAGCAGCCTTCGGAGAGGAAA[A]

AA[A][T]T[T]TTTTGGTTGAACATAACATACTATTGGTAGTTGGAATT

CCAAGTATGAGCACAGAT[T]GAAAGGCATTT[A]TTTGCAAGTCACTTC

CTC[A]TCCTCCTCGAAGTCTTTTGCTTTCACCCTATTGCAGATTCTATG

CCCACTGAAATTCTCTCTGT[AAAAGCTCCA][T]CTTCCAACTCGTCCTCT

GCTGCTCTTTCTTTTTCTTCTCTCTCTTCCTTAGCCAAATCTAGGTCAAA

GGCTAAGTCTAAAAAACCATCCAAAATCAAGGATTCTCTCACATC[C]TC

TGGGTTTCACTTGTTTGTTTAATTCGTTTGTACTTTTGTTTATGATTACT

CTTTTCGCTCTAAGTATAATTCTCATGTACTTTGAGCATTAGTCTCTTTT

GTTAATACATTTAAAGAGGCTCGTATCAATGTTTGGTGCTGACCTCCAAG

GAAATATCCAACAACTTTTAGTTGAGGTGCACTTAAAAATATTTCCCTCA

ATCACTTTGGATACATGCGGTTAAGTCGCTTTTGGCAG-3'
```

The first SNP set indicates polymorphisms such that, for example, the 1st to 9th underlined bases in brackets in SEQ ID NO: 3 are A, A, T, T, T, A, A, T and C, respectively. That is, for example, a melon plant is resistant to powdery mildew when SNP1$_{45}$, SNP1$_{48}$, SNP1$_{49}$, SNP1$_{51}$, SNP1$_{108}$, SNP1$_{120}$, SNP1$_{139}$, SNP1$_{214}$, and SNP1$_{327}$ in the first SNP set are A, A, T, T, T, A, A, T, and C, respectively, and is susceptible to powdery mildew when the combination of the bases is other than the above combination (for example, when they are A, T, T, T, T, A, G, and T or when they are G, A, A, A, G, C, A, C, and T). The relevance of the first SNP set with the powdery mildew resistance has not been reported heretofore. The first SNP set is a novel combination of SNPs discovered first by the inventors of the present invention as being involved in the powdery mildew resistance.

In the condition (2), the resistance locus further may be identified by, for example, the base sequence from positions 204 to 213 (SEQ ID NO: 7: 5'-AAAAGCTCCA-3') in the base sequence of SEQ ID NO: 3. The base sequence of SEQ ID NO: 7 is the boxed base sequence in the base sequence of SEQ ID NO: 3. That is, for example, a melon plant is resistant to powdery mildew when the above-described first SNP set includes the combination of the bases exhibiting the powdery mildew resistance, and also the base sequence of SEQ ID NO: 7 is included in a base sequence corresponding to the base sequence of SEQ ID NO: 3, and is susceptible to powdery mildew when the base sequence of SEQ ID NO: 7 is not included. The relevance of the base sequence of SEQ ID NO: 7 with the powdery mildew resistance has not been reported heretofore. The base sequence of SEQ ID NO: 7 is a novel base sequence discovered first by the inventors of the present invention as being involved in the powdery mildew resistance.

In the present invention, the resistance locus may satisfy one of the conditions (1) and (2) or both the conditions (1) and (2), for example. Preferably, the resistance locus satisfies both the conditions (1) and (2) because the resistance locus shows higher correlation with the powdery mildew resistance.

The resistance locus further may satisfy, as the condition based on the combination of SNPs, at least one of the following conditions (3) and (4), for example.

Condition (3):
The powdery mildew resistance locus on chromosome 6 is identified by polymorphisms of bases at positions 50, 141, and 266 in the base sequence of SEQ ID NO: 4.

SEQ INO: 4
5'-AGGAAACGAAGAATAGACGAAATGTCAAGGTTGCTATTCTAATACCA

TG[C]TTCCCAAGTCAGACCAGCTTCATTCCAGCATATGGTATCAAGAGA

TTCTATTGACGTGACTTCTAATGTCTCTTCCACACC[T]ACTCCAGA[A]AT

TCCCCAATTTCATTTAGATTAACATTTTACAGTCGAATCAATCCCACCAA

CCCAGTCATTTATAATCTGCTAATTTCTGGACTGTGCAACGACAAATCCT

GCACAGACAAGGCCTACGATAG[T]TTGTGCAACCAGACTCCTGACATGA

ATATCCATTCTCCCATTATTGCTGAGATTCATCTCGTATATACTTAATCC

AACTTTCTACATTGCCAAAAAATTTCTGGCCTACAAAGCAAATATGACCC

TAAACTTGAAGAAACCAATATTGTAAAAGCTTTAACTCAACATATGAGGA

GATATTTTTATGCCA[A]ACATAATCAAGAAAAGATAAGCTTCTCTTTCCGG

TTCTCA-3'

Condition (4):
The powdery mildew resistance locus on chromosome 6 is identified by polymorphisms of bases at positions 99, 174, 184, 199, and 200 in the base sequence of SEQ ID NO: 5.

SEQ ID NO: 5
5'-GTTCGGATCGGAAAATTCAATCAAAGGAATAAGCGCTACAAAACAATA

AACACACACATACATCCAAAAATTACAAATCTCCTATCATCATCAAGAAA

[C]AGAAAAACCAAACCGAAAACGAAATAAACGCCAAATAATTTCAGAAAA

TCGATGCGACGGAATAAGAAATGCAT[G]TATCTGGTA[T]GATCGAAAGA

GAAA[A][T]ATACGAGATCCGGTGGTTTGCCAGAGCTGCATCTCGCCGTC

TTCATAATCGCCTTCGGGACGAACGGCGATGAGAACAAGGTAATCGCCCTT

GCGGACAACGTTGTCGATGGCCCATTTGAGGGCTTTAATGCTGCAGGCA

GAGAAATCCACCGCGACGCCGACTCTCCGTTGACCGTCCATGCTTTTTG

TGGGTTGGGATTTTCAGTGCGTTTGAGCTTTGTGGAAGGAAGGAAGAAT

GGAATGAATGTCGGAAAGCTTGG-3'

In the condition (3), the resistance locus is identified by, for example, the combination of three types of SNPs (also referred to as "second SNP set" hereinafter) in the base sequence of SEQ ID NO: 4. The three types of SNPs are, for example, SNPs at positions 50, 141, and 266 in the base sequence of SEQ ID NO: 4. Hereinafter, the SNPs at positions 50, 141, and 266 also are referred to as "$SNP2_{50}$", "$SNP2_{141}$", and "$SNP2_{266}$", respectively. $SNP2_{50}$, $SNP2_{141}$, and $SNP2_{266}$ are the 1st to 3rd underlined bases in brackets in the base sequence of SEQ ID NO: 4, respectively. The base sequence of SEQ ID NO: 4 can be obtained from the melon plant deposited under Accession No. FERM BP-22291 to be described below, for example. The base sequence of SEQ ID NO: 4 corresponds to, for example, the base sequence from positions 6398131 to 6398627 on chromosome 6 in the above-described genome sequence information on melon plants.

The second SNP set indicates polymorphisms such that, for example, the 1st to 3rd underlined bases in brackets in SEQ ID NO: 4 are C, A, and T, respectively. That is, for example, a melon plant is resistant to powdery mildew when $SNP2_{50}$, $SNP2_{141}$, and $SNP2_{266}$ in the second SNP set are C, A, and T, respectively, and is susceptible to powdery mildew when the combination of the bases is other than the above combination (for example, when they are T, T, and A). The relevance of the second SNP set with the powdery mildew resistance has not been reported heretofore. The second SNP set is a novel combination of SNPs discovered first by the inventors of the present invention as being involved in the powdery mildew resistance.

In the condition (3), the resistance locus further may be identified by, for example, the combination of SNPs at positions 132 and 457 in the base sequence of SEQ ID NO: 4. Hereinafter, the SNPs at positions 132 and 457 also are referred to as "$SNP2_{132}$", and "$SNP2_{457}$", respectively. $SNP2_{132}$ and $SNP2_{457}$ are the 1st and 2nd boxed bases in the base sequence of SEQ ID NO: 4, respectively.

$SNP2_{132}$ and $SNP2_{457}$ are polymorphisms such that, for example, the 1st and 2nd underlined boxed bases in SEQ ID NO: 4 are T and A, respectively. That is, for example, a melon plant is resistant to powdery mildew when the above-described second SNP set includes the combination of the bases exhibiting the powdery mildew resistance, and also $SNP2_{132}$ and $SNP2_{457}$ are T and A, respectively, and is susceptible to powdery mildew when the combination of the bases is other than the above combination. The relevance of $SNP2_{132}$ and $SNP2_{457}$ with the powdery mildew resistance has not been reported heretofore. The combination of $SNP2_{132}$ and $SNP2_{457}$ is a novel combination of SNPs discovered first by the inventors of the present invention as being involved in the powdery mildew resistance.

In the condition (4), the resistance locus is identified by, for example, the combination of five types of SNPs (also referred to as "third SNP set" hereinafter) in the base sequence of SEQ ID NO: 5. The five types of SNPs are, for example, SNPs at positions 99, 174, 184, 199, and 200 in the base sequence of SEQ ID NO: 5. Hereinafter, the SNPs at positions 99, 174, 184, 199, and 200 also are referred to as "$SNP3_{99}$", "$SNP3_{174}$", "$SNP3_{184}$", "$SNP3_{199}$", and "$SNP3_{200}$", respectively. $SNP3_{99}$, $SNP3_{174}$, $SNP3_{184}$, $SNP3_{199}$, and $SNP3_{200}$ are the 1st to 5th underlined bases in brackets in the base sequence of SEQ ID NO: 5, respectively. The base sequence of SEQ ID NO: 5 can be obtained from the melon plant deposited under Accession No. FERM BP-22291 to be described below, for example. The base sequence of SEQ ID NO: 5 corresponds to, for example, the base sequence from positions 5269642 to 5270103 on chromosome 6 in the above-described genome sequence information on melon plants.

The third SNP set indicates polymorphisms such that, for example, the 1st to 5th underlined bases in brackets in SEQ ID NO: 5 are C, G, T, A, and T, respectively. That is, for example, a melon plant is resistant to powdery mildew when $SNP3_{99}$, $SNP3_{174}$, $SNP3_{184}$, $SNP3_{199}$, and $SNP3_{200}$ in the third SNP set are C, G, T, A, and T, respectively, and is susceptible to powdery mildew when the combination of the bases is other than the above combination (for example, when they are T, A, C, T, and C). The relevance of the third SNP set with the powdery mildew resistance has not been reported heretofore. The third SNP set is a novel combination of SNPs discovered first by the inventors of the present invention as being involved in the powdery mildew resistance.

When the resistance locus further satisfies at least one of the conditions (3) and (4), the combination of the conditions satisfied by the resistance locus is not particularly limited, and examples thereof include the following combinations.
Combination of the conditions (1) and (3)
Combination of the conditions (1) and (4)
Combination of the conditions (2) and (3)
Combination of the conditions (2) and (4)
Combination of the conditions (1), (2), and (3)
Combination of the conditions (1), (2), and (4)
Combination of the conditions (1), (2), (3) and (4)

While the resistance locus satisfies at least one of the conditions (1) and (2) in the present invention, the resistance locus is not limited thereto. The resistance locus may satisfy at least one of the conditions (3) and (4), instead of at least one of the conditions (1) and (2). In this case, the resistance locus may satisfy one of the conditions (3) and (4) or both the conditions (3) and (4), for example. Preferably, the resistance locus satisfies both the conditions (3) and (4) because the resistance locus shows higher correlation with the powdery mildew resistance.

(ii) Condition Based on Base Sequence(s)

As described in the above item (ii), the resistance locus may satisfy, for example, a condition based on at least one of the base sequence of each of the amplified fragments obtained by amplification using the primer set and a base sequence including the combination of SNPs, and specifically, the resistance locus may satisfy at least one of the following conditions (5) and (6). In the following condition (5), the following polynucleotides (a2) and (a3) are polynucleotides each having a function equivalent to that of the following polynucleotide (a1) regarding the powdery mildew resistance in the resistance locus. In the following condition (6), the following polynucleotides (b2) and (b3) are polynucleotides each having a function equivalent to that of the following polynucleotide (b1) regarding the powdery mildew resistance in the resistance locus.
Condition (5):
The powdery mildew resistance locus on chromosome 6 is identified by the following polynucleotide (a).
(a) the following polynucleotide (a1), (a2), or (a3)
(a1) a polynucleotide consisting of a base sequence of SEQ ID NO: 6

(a2) a polynucleotide consisting of a base sequence obtained by deletion, substitution, insertion, and/or addition of one or more bases in the base sequence of the polynucleotide (a1)
(a3) a polynucleotide consisting of a base sequence having at least 80% sequence identity to the base sequence of the polynucleotide (a1)
Condition (6):
The powdery mildew resistance locus on chromosome 6 is identified by the following polynucleotide (b).
(b) the following polynucleotide (b1), (b2), or (b3)
(b1) a polynucleotide consisting of the base sequence of SEQ ID NO: 3
(b2) a polynucleotide consisting of a base sequence obtained by deletion, substitution, insertion, and/or addition of one or more bases in the base sequence of the polynucleotide (b1) with the base (A) at position 45, the base (A) at position 48, the base (T) at position 49, the base (T) at position 51, the base (T) at position 108, the base (A) at position 120, the base (A) at position 139, the base (T) at position 214, and the base (C) at position 327 in the base sequence of the polynucleotide (b1) being conserved
(b3) a polynucleotide consisting of a base sequence having at least 80% sequence identity to the base sequence of the polynucleotide (b1) with the base (A) at position 45, the base (A) at position 48, the base (T) at position 49, the base (T) at position 51, the base (T) at position 108, the base (A) at position 120, the base (A) at position 139, the base (T) at position 214, and the base (C) at position 327 in the base sequence of the polynucleotide (b1) being conserved In the polynucleotide (a1), the base sequence of SEQ ID NO: 6 is as shown below. The polynucleotide (a1) (the base sequence of SEQ ID NO: 6) is obtained by, for example, amplifying the gene of a melon plant using the primer set 1, for example. The base sequence of SEQ ID NO: 6 is, for example, the base sequence of the amplified fragment including the forward primer 1. The polynucleotide (a1) can be obtained from the melon plant deposited under Accession No. FERM BP-22291 to be described below, for example.

SEQ ID NO: 6
5'-AATCTCAACAAGTGAGCTTTTATTGTAAAAAATACAACACAAGTAAG
AGTGTGTGTATTTATAATTGAAAGAAGAAGAAGAAGAAGAAGAAGAAGAA
GAAAACAAGACAAAAAGAAAATTGAAGATAATCATG-3'

In the polynucleotide (a2), the number of the "one or more" bases is, for example, 1 to 27, 1 to 20, 1 to 15, 1 to 7, 1 to 5, 1 to 4, 1 to 3, 1, or 2. In the present invention, the numerical range regarding the number of bases discloses all the positive integers falling within that range, for example. That is, for example, the description "one to five bases" discloses all of "one, two, three, four, and five bases" (the same applies hereinafter).

In the polynucleotide (a3), the "sequence identity" is, for example, at least 80%, at least 85%, at least 89%, at least 90%, at least 95%, at least 96%, at least 97%, at least 98%, or at least 99%. The "sequence identity" can be determined by aligning two base sequences (the same applies hereinafter).

In the polynucleotide (b1), the 1st to 9th underlined bases in brackets in SEQ ID NO: 3 are bases corresponding to the polymorphisms of $SNP1_{45}$, $SNP1_{48}$, $SNP1_{49}$, $SNP1_{51}$, $SNP1_{108}$, $SNP1_{120}$, $SNP1_{139}$, $SNP1_{214}$, and $SNP1_{327}$, respectively. The polynucleotide (b1) can be obtained from the melon plant deposited under Accession No. FERM BP-22291 to be described below, for example.

In the polynucleotide (b2), the number of the "one or more" bases is, for example, 1 to 112, 1 to 84, 1 to 62, 1 to 56, 1 to 28, 1 to 23, 1 to 17, 1 to 12, 1 to 6, 1 to 3, 1, or 2.

In the polynucleotide (b2), the base sequence from positions 204 to 213 (SEQ ID NO: 7: 5'-AAAAGCTCCA-3') in the base sequence of the polynucleotide (b1) further may be conserved, for example. In this case, the polynucleotide (b2) is, for example, a polynucleotide consisting of a base sequence obtained by deletion, substitution, insertion, and/or addition of one or more bases in the base sequence of the polynucleotide (b1) with the base (A) at position 45, the base (A) at position 48, the base (T) at position 49, the base (T) at position 51, the base (T) at position 108, the base (A) at position 120, the base (A) at position 139, the base (T) at position 214, the base (C) at position 327, and the base sequence from positions 204 to 213 (5'-AAAAGCTCCA-3') in the base sequence of the polynucleotide (b1) being conserved.

In the polynucleotide (b3), the "sequence identity" is, for example, at least 80%, at least 85%, at least 89%, at least 90%, at least 95%, at least 96%, at least 97%, at least 98%, or at least 99%.

In the polynucleotide (b3), the base sequence from positions 204 to 213 (SEQ ID NO: 7: 5'-AAAAGCTCCA-3') in the base sequence of the polynucleotide (b1) further may be conserved, for example. In this case, the polynucleotide (b3) is, for example, a polynucleotide consisting of a base sequence having at least 80% sequence identity to the base sequence of the polynucleotide (b1) with the base (A) at position 45, the base (A) at position 48, the base (T) at position 49, the base (T) at position 51, the base (T) at position 108, the base (A) at position 120, the base (A) at position 139, the base (T) at position 214, the base (C) at position 327, and the base sequence from positions 204 to 213 (5'-AAAAGCTCCA-3') in the base sequence of the polynucleotide (b1) being conserved.

When the resistance locus satisfies at least one of the conditions (5) and (6), the resistance locus may satisfy one of the conditions (5) and (6) or both the conditions (5) and (6), for example. Preferably, the resistance locus satisfies both the conditions (5) and (6) because the resistance locus shows higher correlation with the powdery mildew resistance.

The resistance locus further may satisfy, as the condition based on a base sequence(s), at least one of the following conditions (7) and (8), for example. In the following condition (7), the following polynucleotides (c2) and (c3) are polynucleotides each having a function equivalent to that of the following polynucleotide (c1) regarding the powdery mildew resistance in the resistance locus. In the following condition (8), the following polynucleotides (d2) and (d3) are polynucleotides each having a function equivalent to that of the following polynucleotide (d1) regarding the powdery mildew resistance in the resistance locus.

Condition (7):
The powdery mildew resistance locus on chromosome 6 is identified by the following polynucleotide (c).
(c) the following polynucleotide (c1), (c2), or (c3)
(c1) a polynucleotide consisting of the base sequence of SEQ ID NO: 4
(c2) a polynucleotide consisting of a base sequence obtained by deletion, substitution, insertion, and/or addition of one or more bases in the base sequence of the polynucleotide (c1) with the base (C) at position 50, the base (A) at position 141, and the base (T) at position 266 in the base sequence of the polynucleotide (c1) being conserved (c3) a polynucleotide consisting of a base sequence having at least 80% sequence identity to the base sequence of the polynucleotide (c1) with the base (C) at position 50, the base (A) at position 141, and the base (T) at position 266 in the base sequence of the polynucleotide (c1) being conserved.

Condition (8):
The powdery mildew resistance locus on chromosome 6 is identified by the following polynucleotide (d).
(d) the following polynucleotide (d1), (d2), or (d3)
(d1) a polynucleotide consisting of the base sequence of SEQ ID NO: 5
(d2) a polynucleotide consisting of a base sequence obtained by deletion, substitution, insertion, and/or addition of one or more bases in the base sequence of the polynucleotide (d1) with the base (C) at position 99, the base (G) at position 174, the base (T) at position 184, the base (A) at position 199, and the base (T) at position 200 in the base sequence of the polynucleotide (d1) being conserved
(d3) a polynucleotide consisting of a base sequence having at least 80% sequence identity to the base sequence of the polynucleotide (d1) with the base (C) at position 99, the base (G) at position 174, the base (T) at position 184, the base (A) at position 199, and the base (T) at position 200 in the base sequence of the polynucleotide (d1) being conserved In the polynucleotide (c1), the 1st to 3rd underlined bases in brackets in SEQ ID NO: 4 are bases corresponding to the polymorphisms of $SNP2_{50}$, $SNP2_{141}$, and $SNP2_{266}$, respectively. The polynucleotide (c1) can be obtained from the melon plant deposited under Accession No. FERM BP-22291 to be described below, for example.

In the polynucleotide (c2), the number of the "one or more" bases is, for example, 1 to 100, 1 to 75, 1 to 55, 1 to 50, 1 to 25, 1 to 20, 1 to 15, 1 to 10, 1 to 5, 1 to 3, 1, or 2.

In the polynucleotide (c2), for example, the base (T) at position 132 and the base (A) at position 457 in the polynucleotide (c1) further may be conserved. In this case, the polynucleotide (c2) is, for example, a polynucleotide consisting of a base sequence obtained by deletion, substitution, insertion, and/or addition of one or more bases in the base sequence of the polynucleotide (c1) with the base (C) at position 50, the base (T) at position 132, the base (A) at position 141, the base (T) at position 266, and the base (A) at position 457 in the base sequence of the polynucleotide (c1) being conserved.

In the polynucleotide (c3), the "sequence identity" is, for example, at least 80%, at least 85%, at least 89%, at least 90%, at least 95%, at least 96%, at least 97%, at least 98%, or at least 99%.

In the polynucleotide (c3), for example, the base (T) at position 132 and the base (A) at position 457 in the polynucleotide (c1) further may be conserved. In this case, the polynucleotide (c3) is, for example, a polynucleotide consisting of a base sequence having at least 80% sequence identity to the base sequence of the polynucleotide (c1) with the base (C) at position 50, the base (T) at position 132, the base (A) at position 141, the base (T) at position 266, and the base (A) at position 457 in the base sequence of the polynucleotide (c1) being conserved.

In the polynucleotide (d1), the 1st to 5th underlined bases in brackets in SEQ ID NO: 5 are bases corresponding to the polymorphisms of $SNP3_{99}$, $SNP3_{174}$, $SNP3_{184}$, $SNP3_{199}$, and $SNP3_{200}$, respectively. The polynucleotide (d1) can be obtained from the melon plant deposited under Accession No. FERM BP-22291 to be described below, for example.

In the polynucleotide (d2), the number of the "one or more" bases is, for example, 1 to 93, 1 to 70, 1 to 51, 1 to 48, 1 to 24, 1 to 19, 1 to 15, 1 to 10, 1 to 5, 1 to 3, 1, or 2.

In the polynucleotide (d3), the "sequence identity" is, for example, at least 80%, at least 85%, at least 89%, at least 90%, at least 95%, at least 96%, at least 97%, at least 98%, or at least 99%.

When the resistance locus further satisfies at least one of the conditions (7) and (8), the combination of the conditions satisfied by the resistance locus is not particularly limited, and examples thereof include the following combinations.
Combination of the conditions (5) and (7)
Combination of the conditions (5) and (8)
Combination of the conditions (6) and (7)
Combination of the conditions (6) and (8)
Combination of the conditions (5), (6), and (7)
Combination of the conditions (5), (6), and (8)
Combination of the conditions (5), (6), (7) and (8)

While the resistance locus satisfies "(i) Condition based on length of amplified fragment and combination of SNPs" in the present invention, the resistance locus is not limited thereto. As described above, the resistance locus may satisfy "(ii) Condition based on base sequence(s)", instead of "(i) Condition based on length of amplified fragment and combination of SNPs." In this case, the resistance locus may satisfy, for example, at least one of the conditions (7) and (8), instead of at least one of the conditions (5) and (6). Also, in this case, the resistance locus may satisfy one of the conditions (7) and (8) or both the conditions (7) and (8), for example. Preferably, the resistance locus satisfies both the conditions (7) and (8) because the resistance locus shows higher correlation with the powdery mildew resistance.

(iii) Condition Based on Base Sequence of Region

As described in the above item (iii), the resistance locus may satisfy, for example, the condition based on the base sequence of a region including at least one of the base sequence of each of the amplified fragments obtained by amplification using the primer set and a base sequence including the combination of SNPs, and specifically, the resistance locus may satisfy the following condition (9). The region may include the whole or part of at least one of the base sequence of the amplified fragment and the base sequence including the combination of SNPs, for example.
Condition (9):
The powdery mildew resistance locus on chromosome 6 is identified by a base sequence between sites of two SNPs selected from the group consisting of the following SNP (A), SNP (B), and SNP (C) on the chromosome.
(A) one SNP selected from the group consisting of SNPs at positions 45, 48, 49, 51, 108, 120, 139, 214, and 327 in the base sequence of SEQ ID NO: 3
(B) one SNP selected from the group consisting of SNPs at positions 50, 132, 141, 266, and 457 in the base sequence of SEQ ID NO: 4
(C) one SNP selected from the group consisting of SNPs at positions 99, 174, 184, 199, and 200 in the base sequence of SEQ ID NO: 5

Regarding SNP (A), the SNPs at positions 45, 48, 49, 51, 108, 120, 139, 214, and 327 are, for example, bases corresponding to the polymorphisms of $SNP1_{46}$, $SNP1_{48}$, $SNP1_{49}$, $SNP1_{51}$, $SNP1_{108}$, $SNP1_{120}$, $SNP1_{139}$, $SNP1_{214}$, and $SNP1_{327}$, respectively.

Regarding SNP (B), the SNPs at positions 50, 132, 141, 266, and 457 are, for example, bases corresponding to the polymorphisms of $SNP2_{50}$, $SNP2_{132}$, $SNP2_{141}$, $SNP2_{266}$, and $SNP2_{457}$, respectively.

Regarding SNP (C), the SNPs at positions 99, 174, 184, 199, and 200 are, for example, bases corresponding to the polymorphisms of $SNP3_{99}$, $SNP3_{174}$, $SNP3_{184}$, $SNP3_{199}$, and $SNP3_{200}$, respectively.

The upstream-side end and the downstream-side end of the region can be identified by, for example, the sites of two SNPs selected from the group consisting of SNPs (A), (B) and (C), as described above. The region is not limited as long as it is located between the sites of two SNPs selected from the group consisting of SNPs (A), (B) and (C), for example, and may or may not include both or one of the sites of the two SNPs, for example. When the region includes the sites of the SNPs, the upstream-side end and the downstream-side end of the region are the sites of the SNPs. The bases at the upstream-side end and the downstream-side end may each be an underlined or boxed base in the above base sequences or may be a base other than the underlined base and the boxed bases in the above base sequences, for example.

Specifically, the SNPs at the upstream-side end and the downstream-side end can be determined on the basis of the chromosomal locations of SNPs (A), (B) and (C), for example. For example, as shown in FIG. 1, SNPs (A), (B) and (C) are located on chromosome 6 of a melon plant in the order of SNP (C), SNP (A), and SNP (B) from the upstream side ($SNP3_{99}$) toward the downstream side ($SNP2_{457}$). Also, as shown in FIG. 1, the base sequence that forms the amplified fragment when amplified is located between SNP (A) and SNP (B), for example. In this case, examples of the combination of the two SNPs identifying the region include the following combinations.
Combination of SNP (A) and SNP (B)
Combination of SNP (A) and SNP (C)
Combination of SNP (B) and SNP (C)
Among these combinations, for example, the following combination is preferable because the resistance locus shows higher correlation with the powdery mildew resistance.
Combination of SNP (B) and SNP (C)

When the resistance locus is identified by the base sequence of a region between sites of two SNPs, it is preferable that the resistance locus further satisfies the above-described condition(s) relevant to the base sequence of the region. Specifically, it is preferable that the resistance locus satisfies, in the base sequence of the region, at least one of the conditions (1) and (2), for example. Also, it is preferable that the resistance locus further satisfies, in the base sequence of the region, at least one of the conditions (3) and (4), for example.

The relevant condition may be, for example, a condition relevant to the base sequence between the sites of the SNPs at the upstream-side and downstream-side ends identifying the region, and can be determined as appropriate on the basis of, for example, the chromosomal locations of SNPs (A), (B) and (C) and the base sequence that forms the amplified fragment when amplified shown in FIG. 1. The number of the relevant conditions may be one or more, for example. As a specific example, all the conditions relevant to the base sequence located between the sites of the SNPs identifying the region may be used as the relevant conditions.

The combination of the base sequence between the sites of two SNPs in the region and the condition(s) relevant to the base sequence of the region to be satisfied by the resistance locus is not particularly limited, and may be the following condition (a), (b) or (c), for example.
Condition (a):
The powdery mildew resistance locus on chromosome 6 includes the base sequence of a region between the sites of SNP (A) and SNP (B) on the chromosome, and satisfies at least one of the conditions (1) and (2).

Condition (b):
The powdery mildew resistance locus on chromosome 6 includes the base sequence of a region between the sites of SNP (B) and SNP (C) on the chromosome, and satisfies at least one of the conditions (1) and (2).
Condition (c):
The powdery mildew resistance locus on chromosome 6 includes the base sequence of a region between the sites of SNP (B) and SNP (C) on the chromosome, and satisfies at least one of the conditions (1) and (2) and at least one of the conditions (3) and (4).

In the condition (a), the resistance locus may satisfy one of the conditions (1) and (2) or both the conditions (1) and (2), for example.

In the condition (b), the resistance locus may satisfy one of the conditions (1) and (2) or both the conditions (1) and (2), for example.

In the condition (c), the combination of the conditions to be satisfied by the resistance locus is not particularly limited, and examples thereof include the following combinations.
Combination of the conditions (1) and (3)
Combination of the conditions (1) and (4)
Combination of the conditions (2) and (3)
Combination of the conditions (2) and (4)
Combination of the conditions (1), (2), and (3)
Combination of the conditions (1), (2), and (4)
Combination of the conditions (1), (2), (3) and (4)

The resistance marker according to the present invention can confer powdery mildew resistance to melon plants, for example. In the present invention, the degree of the powdery mildew resistance of a melon plant can be expressed by the disease index with reference to the method described in the following Reference Document 2, for example. Regarding the calculation of the disease index according to this method, the explanation in Example 1 to be described below can be referred to, and the disease index of 1 or less can be evaluated as being tolerant (resistant) to powdery mildew and the disease index of 2 or more can be evaluated as being susceptible to powdery mildew, for example.
Reference Document 2: LongZhou Liu et al., "A Sequence-amplified Characterized Region Marker for a Single, Dominant Gene in Melon PI 134198 that Confers Resistance to a Unique Race of *Podosphaera xanthii* in China", HORTSCIENCE, 2010, vol. 45, No. 9, pp. 1407-1410

The resistance marker according to the present invention may further include a marker for any other resistance, for example.

2. Powdery Mildew Resistant Melon Plant

The powdery mildew resistant melon plant of the present invention is, as described above, a powdery mildew resistant melon plant including: a powdery mildew resistance locus on chromosome 6 in a homozygous form, wherein the powdery mildew resistance locus on chromosome 6 satisfies at least one of the following conditions (1) and (2).
Condition (1):
The powdery mildew resistance locus on chromosome 6 is identified by a length of an amplified fragment obtained by amplification using the following primer set 1, and the length of the amplified fragment is 133 bp or more.
Primer Set 1:
   a forward primer 1 consisting of a base sequence of SEQ ID NO: 1
   a reverse primer 1 consisting of a base sequence of SEQ ID NO: 2

Condition (2):
The powdery mildew resistance locus on chromosome 6 is identified by polymorphisms of bases at positions 45, 48, 49, 51, 108, 120, 139, 214, and 327 in a base sequence of SEQ ID NO: 3.

The powdery mildew resistant melon plant of the present invention is characterized in that it includes a powdery mildew resistance locus on chromosome 6 in a homozygous form and that the powdery mildew resistance locus on chromosome 6 satisfies at least one of the conditions (1) and (2). Other configurations or conditions are not particularly limited. The powdery mildew resistant melon plant of the present invention includes the resistance marker of the present invention as the resistance locus. Thus, for example, the above description regarding the resistance marker of the present invention also applies to the powdery mildew resistant melon plant of the present invention. In the present invention, the powdery mildew resistance locus on chromosome 6 should be interpreted as interchangeable with the resistance locus in the resistance marker of the present invention, for example. The above descriptions regarding the resistance marker of the present invention, etc., also apply to the powdery mildew resistant melon plant of the present invention, for example.

The powdery mildew resistant melon plant of the present invention is resistant to powdery mildew.

In the powdery mildew resistant melon plant of the present invention, the powdery mildew resistance is conferred by the above-described resistance locus. While the powdery mildew resistant melon plant of the present invention includes the resistance locus on chromosome 6 in a homozygous form, the powdery mildew resistant melon plant may include the resistance locus on chromosome 6 on, instead of on chromosome 6, any chromosome other than chromosome 6, for example. That is, the powdery mildew resistant melon plant may include the resistance locus on chromosome 6 on any of chromosome 1, chromosome 2, chromosome 3, chromosome 4, chromosome 5, chromosome 7, chromosome 8, chromosome 9, chromosome 10, chromosome 11, and chromosome 12. When the powdery mildew resistant melon plant includes the resistance marker on any chromosome other than chromosome 6, the powdery mildew resistant melon plant may include one resistance locus on a chromosome other than chromosome 6 or two resistance loci on a chromosome(s) other than chromosome 6, for example. In the latter case, the powdery mildew resistant melon plant may include the two resistance loci on the same chromosome or on different chromosomes, for example. As described above, the "chromosome" also can be referred to as "linkage group", for example, and reference can be made to the above description regarding the chromosome and the linkage group.

In the powdery mildew resistant melon plant of the present invention, the above description regarding the resistance marker of the present invention also applies to the resistance locus, for example.

The powdery mildew resistant melon plant of the present invention may satisfy one of the conditions (1) and (2) or both the conditions (1) and (2), for example. Preferably, the powdery mildew resistant melon plant satisfies both the conditions (1) and (2) because the powdery mildew resistant melon plant shows higher correlation with the powdery mildew resistance.

The powdery mildew resistant melon plant of the present invention may be, for example, the melon plant deposited under Accession No. FERM BP-22291 (*Cucumis melo*) or a progeny line thereof. The deposited melon plant includes the resistance locus on chromosome 6 in a homozygous form, for example. The information on the deposit is as follows.
Type of deposit: International deposit
Name of depository institution: National Institute of Technology and Evaluation; NITE-IPOD
Address: 2-5-8-120, Kazusakamatari, Kisarazu-shi, Chiba 292-0818, Japan Accession No. FERM BP-22291
Identifying designation: Takii8
Date of acceptance: Aug. 14, 2015

The powdery mildew resistant melon plant according to the present invention also can be produced by, for example, introducing the resistance locus to a melon plant. The method for introducing the resistance locus to a melon plant is not particularly limited, and a conventionally known genetic engineering procedure may be used, for example. The resistance locus to be introduced may be the above-described powdery mildew resistance locus, for example.

The characteristics of the powdery mildew resistant melon plant of the present invention other than the powdery mildew resistance, such as, for example, morphological characteristics and biological characteristics, are not particularly limited.

The powdery mildew resistant melon plant of the present invention also may have any other resistance.

The term "plant body" as used in the present invention may refer to either a plant individual representing the whole plant or a part of the plant individual. The part of the plant individual may be any of organs, tissues, cells, and propagules, for example. Examples of the organs include petals, corollas, flowers, leaves, seeds, fruits, stems, and roots. The tissue is a part of the organ, for example. The part of the plant body may be one type of organ, tissue, and/or cell, or two or more types of organs, tissues, and/or cells, for example.

3. Method for Producing Powdery Mildew Resistant Melon Plant

Next, the method for producing a powdery mildew resistant melon plant according to the present invention (also referred to simply as "production method" hereinafter) will be described. The methods to be described below are merely illustrative, and the present invention is by no means limited to these methods. In the present invention, the production method also can be referred to as "growing method", for example. Also, in the present invention, the powdery mildew resistance locus should be interpreted as interchangeable with the resistance marker according to the present invention.

As described above, the method for producing a powdery mildew resistant melon plant according to the present invention includes the following steps (a) and (b):
(a) crossing the powdery mildew resistant melon plant according to the present invention with another melon plant; and
(b) selecting a powdery mildew resistant melon plant from one or more melon plants obtained in the step (a) or progeny lines thereof.

The production method according to the present invention is characterized in that the powdery mildew resistant melon plant according to the present invention is used as a parent, and other steps or conditions are not particularly limited. The above descriptions regarding the resistance marker of the present invention, etc., also apply to the production method of the present invention, for example. As described above, the powdery mildew resistance locus can confer the powdery mildew resistance while it is a single gene locus, for example. Thus, according to the production method of the present invention, for example, by using the resistance locus, progenies exhibiting powdery mildew resistance can be obtained easily also from F1 produced by crossing the powdery mildew resistant melon plant of the present invention with other melon plants or progenies thereof.

In the step (a), a powdery mildew resistant melon plant used as a first parent is not limited as long as it is the powdery mildew resistant melon plant of the present invention. The powdery mildew resistant melon plant preferably is the above-described melon plant deposited under Accession No. FERM BP-22291 or a progeny line thereof, for example. The powdery mildew resistant melon plant used as the first parent in the step (a) also can be obtained by the screening method of the present invention to be described below, for example. Thus, it is possible to provide the powdery mildew resistant melon plant by, for example, selecting it from one or more melon plants to be examined (also referred to as "candidate melon plants") by the following step (x) prior to the step (a), for example:
(x) selecting the powdery mildew resistant melon plant of the present invention from one or more melon plants to be examined.

In the step (x), the selection of the powdery mildew resistant melon plant can be referred to as selection of the melon plant including the resistance locus. Thus, the step (x) can be carried out by the following steps (x1) and (x2), for example.
(x1) detecting the presence or absence of a powdery mildew resistance locus in a homozygous form on chromosomes of each of the one or more melon plants to be examined; and
(x2) selecting one or more melon plants to be examined having the powdery mildew resistance locus in a homozygous form as a powdery mildew resistant melon plant.

As described above, the selection in the step (x) is selection of a melon plant including the powdery mildew resistance locus, for example. Specifically, the powdery mildew resistant melon plant can be selected by carrying out detection of the powdery mildew resistance locus with respect to the one or more melon plants to be examined. As described above in connection with the resistance marker of the present invention, the powdery mildew resistance locus can be detected by using, for example, any of (i) to (iii) or any combination of (i) to (iii) satisfied by the resistance locus: "(i) Condition based on length of amplified fragment and combination of SNPs"; "(ii) Condition based on base sequence(s)"; and "(iii) Condition based on base sequence of region."

The selection in the step (x) will be described with reference to the following specific example. It is to be noted, however, that the present invention is not limited thereto. The description regarding the powdery mildew resistance locus provided above in connection with the resistance marker of the present invention also applies to the powdery mildew resistance locus in the production method of the present invention.

The selection in the step (x) is, for example, selection of a powdery mildew resistant melon plant including a powdery mildew resistance locus on chromosome 6 in a homozygous form, and the powdery mildew resistance locus on chromosome 6 satisfies at least one of the conditions (1) and (2).

In the step (x), the resistance locus is selected by, for example, (i) the condition based on at least one of the length of each of the amplified fragments obtained by amplification using the primer set and the combination of SNPs, as described above. Further, as will be described below, the resistance locus may be selected by, for example, (ii) the condition based on at least one of the base sequence of each of the amplified fragments obtained by amplification using the primer set and a base sequence including the combination of SNPs, (iii) the condition based on the base sequence of a region including at least one of the base sequence of each of the amplified fragments obtained by amplification using the primer set and a base sequence including the combination of SNPs, or any combination of these conditions. When the resistance locus is selected by a combination of these conditions, the combination is not particularly limited, and examples thereof include the following combinations. While the resistance locus is selected by (i), for example, the present invention is not limited thereto. For example, instead of (i), the resistance locus may be selected by (ii) or (iii), or by the combination of (ii) and (iii).
Combination of (i) and (ii)
Combination of (i) and (iii)
Combination of (i), (ii), and (iii)

(i) Selection by Condition Based on Length of Amplified Fragment and Combination of SNPs In the resistance locus, (i) the condition based on the length of the amplified fragment and/or the combination of SNPs to be used for the selection is not particularly limited, and the description in the section "(i) Condition based on length of amplified fragment and combination of SNPs" provided above in connection with the resistance marker of the present invention also applies thereto, for example.

As a specific example, the selection in the step (x) may be, for example, selection of a powdery mildew resistant melon plant that satisfies one of the conditions (1) and (2) or a powdery mildew resistant melon plant that satisfies both the conditions (1) and (2). In the condition (2), the resistance locus further may be identified by, for example, the base sequence from positions 204 to 213 in the base sequence of SEQ ID NO: 3 (SEQ ID NO: 7: 5'-AAAAGCTCCA-3').

Further, in the step (x), the resistance locus further may satisfy, as the condition based on the combination of SNPs, at least one of the conditions (3) and (4), for example. In the condition (3), the resistance locus further may be identified by, for example, the combination of SNPs at positions 132 and 457 in the base sequence of SEQ ID NO: 4.

When the resistance locus further satisfies at least one of the conditions (3) and (4), the combination of the conditions satisfied by the resistance locus is not particularly limited, and examples thereof include the combinations given above as examples in the description regarding the resistance marker of the present invention.

While the resistance locus satisfies, for example, at least one of the conditions (1) and (2) in the production method of the present invention, the resistance locus is not limited thereto. The resistance locus may satisfy at least one of the conditions (3) and (4), instead of at least one of the conditions (1) and (2). In this case, the resistance locus may satisfy one of the conditions (3) and (4) or both the conditions (3) and (4), for example. Preferably, the resistance locus satisfies both the conditions (3) and (4) because the resistance locus shows higher correlation with the powdery mildew resistance.

(ii) Selection by Condition Based on Base Sequence(s)

The selection in the step (x) is, for example, selection of a powdery mildew resistant melon plant including the powdery mildew resistance locus on chromosome 6 in a homozygous form, and the powdery mildew resistance locus on chromosome 6 may satisfy at least one of the conditions (5) and (6). In the resistance locus, (ii) the condition based on the base sequence(s) to be used for the selection is not particularly limited, and the description in the section "(ii) Condition based on base sequence(s)" provided above in connection with the resistance marker of the present invention also applies thereto, for example.

As a specific example, the selection in the step (x) may be, for example, selection of a powdery mildew resistant melon plant that satisfies one of the conditions (5) and (6) or a powdery mildew resistant melon plant that satisfies both the conditions (5) and (6).

In the condition (6), the polynucleotide (b2) may be such that, for example, the base sequence from positions 204 to 213 (SEQ ID NO: 7: 5'-AAAAGCTCCA-3') in the base sequence of the polynucleotide (b1) is further conserved. In the condition (6), the polynucleotide (b3) may be such that, for example, the base sequence from positions 204 to 213 (SEQ ID NO: 7: 5'-AAAAGCTCCA-3') in the base sequence of the polynucleotide (b1) is further conserved.

Further, in the step (x), the resistance locus further may satisfy, as the condition based on a base sequence(s), at least one of the conditions (7) and (8) for example. In the condition (7), the polynucleotide (c2) may be such that, for example, the base (T) at position 132 and the base (A) at position 457 in the base sequence of the polynucleotide (c1) are further conserved. In the condition (7), the polynucleotide (c3) may be such that, for example, the base (T) at position 132 and the base (A) at position 457 in the base sequence of the polynucleotide (c1) are further conserved.

When the resistance locus further satisfies at least one of the conditions (7) and (8), the combination of the conditions satisfied by the resistance locus is not particularly limited, and examples thereof include the combinations given above as examples in the description regarding the resistance marker of the present invention.

(iii) Selection by Condition Based on Base Sequence in Region

The selection in the step (x) is, for example, selection of a powdery mildew resistant melon plant including the powdery mildew resistance locus on chromosome 6 in a homozygous form, and the powdery mildew resistance locus on chromosome 6 may satisfy the condition (9). In the resistance locus, (iii) the condition based on the base sequence of the region to be used for the selection is not particularly limited, and the description in the section "(iii) Condition based on base sequence in region" provided above in connection with the resistance marker of the present invention also applies thereto, for example.

As a specific example, it is preferable that the resistance locus satisfies, in the base sequence of the region, at least one of the conditions (1) and (2), for example. Also, it is preferable that the resistance locus further satisfies, in the base sequence of the region, at least one of the conditions (3) and (4), for example.

Also, the resistance locus may satisfy the above-described condition (a), (b), or (c), for example.

The chromosome to be subjected to the detection of the presence or absence of the resistance locus in a homozygous form preferably is chromosome 6.

In the step (a), the other melon plant to be used as the parent is not particularly limited, and may be, for example, a melon plant carrying a known powdery mildew resistance gene, a melon plant having any other resistance, or the powdery mildew resistant melon plant of the present invention.

In the step (a), the method for crossing the powdery mildew resistant melon plant with the other melon plant is not particularly limited, and a known method can be employed.

In the step (b), melon plants from which a powdery mildew resistant melon plant is to be selected may be the melon plants obtained in the step (a) or progeny lines obtained from these melon plants, for example. Specifically, for example, the melon plants from which a powdery mildew resistant melon plant is to be selected may be the F1 melon plants obtained by the crossing in the step (a) or their progeny lines. The progeny line may be a selfed progeny or a backcross progeny of the F1 melon plant obtained by the crossing in the step (a), or may be a melon plant obtained by crossing the F1 melon plant with another melon plant, for example.

In the step (b), the selection of a powdery mildew resistant melon plant can be achieved by, for example, examining the powdery mildew resistance directly or indirectly.

In the step (b), the direct examination can be carried out by evaluating the powdery mildew of the obtained F1 melon plant or a progeny line thereof on the basis of the above-described disease index, for example. Specifically, for example, the direct examination can be carried out by inoculating the F1 melon plant or the progeny line thereof with powdery mildew fungus and evaluating the powdery mildew resistance on the basis of the disease index. In this case, for example, the F1 melon plant or the progeny line showing the disease index of 1 or less can be selected as a powdery mildew resistant melon plant.

In the step (b), the selection by the indirect examination can be achieved by the following steps (b1) and (b2), for example:
(b1) detecting the presence or absence of the powdery mildew resistance locus in a homozygous form on the chromosomes of each of the one or more melon plants obtained in the step (a) or progeny lines thereof and
(b2) selecting the one or more melon plants obtained in the step (a) or progeny lines thereof having the powdery mildew resistance locus as a powdery mildew resistant melon plant (s).

The selection of the powdery mildew resistant melon plant(s) in the step (b) can be performed in the same manner as in the step (x), namely, by detecting the presence or absence of the powdery mildew resistance locus in a homozygous form, for example. More specifically, the selection can be performed by detecting the presence or absence of the powdery mildew resistance locus in a homozygous form using the molecular marker.

The production method of the present invention preferably further includes growing the powdery mildew resistant melon plant selected in the step (b).

The melon plant or the progeny line demonstrated to be powdery mildew resistant in the above-described manner can be selected as the powdery mildew resistant melon plant.

The production method of the present invention further may include the step of collecting seeds from the progeny line obtained by the crossing.

4. Screening Method for Powdery Mildew Resistant Melon Plants

The screening method for powdery mildew resistant melon plants according to the present invention (also referred to simply as "screening method" hereinafter) is a screening method including the step of as a parent for producing a powdery mildew resistant melon plant by crossing, selecting a powdery mildew resistant melon plant including, as a powdery mildew resistance marker for melon plants, a powdery mildew resistance locus on chromosome 6 in a homozygous form from one or more melon plants to be examined, wherein the powdery mildew resistance locus on chromosome 6 satisfies at least one of the conditions (1) and (2):

Condition (1):
The powdery mildew resistance locus on chromosome 6 is identified by a length of an amplified fragment obtained by amplification using the following primer set 1, and the length of the amplified fragment is 133 bp or more.
Primer set 1:
   a forward primer consisting of a base sequence of SEQ ID NO: 1
   a reverse primer consisting of a base sequence of SEQ ID NO: 2
Condition (2):
The powdery mildew resistance locus on chromosome 6 is identified by polymorphisms of bases at positions 45, 48, 49, 51, 108, 120, 139, 214, and 327 in a base sequence of SEQ ID NO: 3.

The screening method according to the present invention is characterized in that it includes the step of selecting a powdery mildew resistant melon plant including, as a powdery mildew resistance marker for melon plants, a powdery mildew resistance locus on chromosome 6 in a homozygous form from one or more melon plants to be examined and that the powdery mildew resistance locus on chromosome 6 satisfies at least one of the conditions (1) and (2). Other steps or conditions are not particularly limited. According to the screening method of the present invention, a powdery mildew resistant parent can be obtained by using the resistance marker of the present invention. The above descriptions regarding the resistance marker of the present invention, etc., also apply to the screening method of the present invention, for example.

To the selection of the parent, the explanation for the step (x) provided above in connection with the method for producing a powdery mildew resistant melon plant according to the present invention also applies, for example.

EXAMPLES

The present invention will be described specifically below with reference to examples. It is to be noted, however, that the present invention is by no means limited to embodiments described in the following examples.

Example 1

The present example analyzed the mode of inheritance of a powdery mildew resistance locus in novel powdery mildew resistant melon plants, identified the powdery mildew resistance locus, and examined the correlation between the powdery mildew resistance locus and the powdery mildew resistance, in order to examine whether the powdery mildew resistance locus serves as a powdery mildew resistance marker for melon plants, whether melon plants including the resistance locus are resistant to powdery mildew, and whether screening for powdery mildew resistant melon plants can be performed using the powdery mildew resistance marker for melon plants.

(1) Deposited Line

In order to develop novel melon plants resistant to powdery mildew, a large amount of seeds collected from melon lines obtained by subculture breeding in a farm owned by TAKII & CO., LTD. were subjected to breeding, and the powdery mildew resistance of the resultant melon lines was examined. As a result, novel powdery mildew resistance melon lines (*Cucumis melo*) exhibiting powdery mildew resistance were obtained (also referred to as "produced" hereinafter). These novel powdery mildew resistant melon plants were deposited under Accession No. FERM BP-22291. Hereinafter, these powdery mildew resistant melon plants are referred to as a "deposited line."

(2) Mode of Inheritance of Powdery Mildew Resistance

Melon plants of the deposited line (Accession No. FERM BP-22291) were crossed with powdery mildew susceptible melon plants "Harukei No. 3" (available from the NARO Genebank as a plant registered under Accession No. JP32097, *Cucumis melo*) (also referred to as "susceptible melon plants" hereinafter), whereby an F2 segregating population made up of 61 individuals (also referred to as "61 lines" hereinafter) was produced. Further, a powdery mildew fungus inoculation test was carried out in the following manner using the 61 lines. Each individual of the deposited line includes $SNP1_{45}$, $SNP1_{48}$, $SNP1_{49}$, $SNP1_{51}$, $SNP1_{108}$, $SNP1_{120}$, $SNP1_{139}$, $SNP1_{214}$, and $SNP1_{327}$; $SNP2_{50}$, $SNP2_{132}$, $SNP2_{141}$, $SNP2_{266}$, and $SNP2_{457}$; and $SNP3_{99}$, $SNP3_{174}$, $SNP3_{184}$, $SNP3_{199}$, and $SNP3_{200}$ on chromosome 6 in a resistant-type homozygous form. That is, the deposited line is a melon plant that satisfies the conditions (1) to (9). The deposited line is such that two copies of chromosome 6 include the base sequence from positions 204 to 213 in the base sequence of SEQ ID NO: 3 and the length of each of amplified fragments obtained by amplification using the primer set is 133 bp. On the other hand, each of the susceptible melon plants includes $SNP1_{46}$, $SNP1_{48}$, $SNP1_{49}$, $SNP1_{51}$, $SNP1_{108}$, $SNP1_{120}$, $SNP1_{139}$, $SNP1_{214}$, and $SNP1_{327}$; $SNP2_{50}$, $SNP2_{132}$, $SNP2_{141}$, $SNP2_{266}$, and $SNP2_{467}$; and $SNP3_{99}$, $SNP3_{174}$, $SNP3_{184}$, $SNP3_{199}$, and $SNP3_{200}$ on chromosome 6 in a susceptible-type homozygous form. The susceptible melon plant is such that two copies of chromosome 6 do not include the base sequence from positions 204 to 213 in the base sequence of SEQ ID NO: 3 and the length of each of amplified fragments obtained by amplification using the primer set is 132 bp. That is, the susceptible melon plant is a melon plant that does not satisfy the conditions (1) to (9).

The powdery mildew fungus inoculation test was carried out in the following manner with reference to the method described in the above Reference Document 2.

The powdery mildew fungus line 1 (race 3.5) was cultured on a melon plant ("OTOME NO INORI", TAKII & CO., LTD.) grown in an isolated culture device. The fungal flora of the powdery mildew fungus on leaves of the melon plant was scraped from the leaves, and conidia of the powdery mildew fungus were collected. Thereafter, sterile distilled water was added to the conidia. A suspension obtained after adding the sterile distilled water was filtered through a KimWipes® wiper, and the filtrate was collected. Further, a conidial suspension was prepared by diluting the filtrate with sterile distilled water to achieve a concentration of $5 \times 10^4$ conidia/ml. The thus-obtained conidial suspension was used as an inoculum. The 61 lines were seeded on smoked rice hulls beforehand, and then potted into $\frac{1}{10000}$ a Wagner pots filled with sterilized soil. In the inoculation test, the melon plants with the third true leaf being expanded were used. The conidial suspension was sprayed uniformly onto the entire melon plants using a hand spray. Thereafter, the melon plants were grown for 2 weeks in an environment control room under the following conditions: 20° C. to 25° C., a humidity from 60% to 80%, 14000 Lux, and a day length of 12 hours. Then, regarding the grown melon plants, disease investigation was carried out in the following manner. Also, disease investigation was carried out in the same manner with respect to 10 individuals selected from the deposited line and 10 lines of the susceptible melon plants. The race of the powdery mildew fungus was determined on the basis of the following Reference Document 3.

Reference Document 3: Fernando J. Yuste-Lisbona et al., "Codominant PCR-based markers and candidate genes for powdery mildew resistance in melon (*Cucumis melo* L.)", Theor. Appl. Genet., 2011, vol. 122, pp. 747-758

Figure 2A:
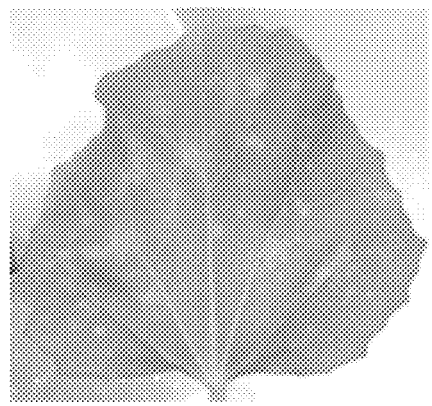
FIGS. 2A to 2D show photographs illustrating criteria for evaluating the disease index of melon plants in Example 1.
Figure 2B:
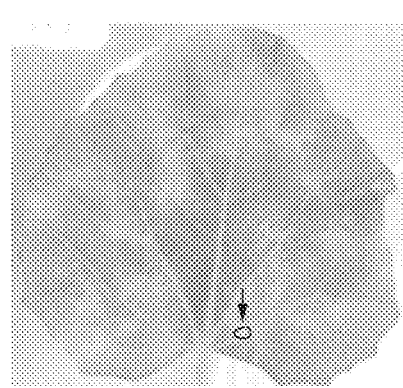
Figure 2C:
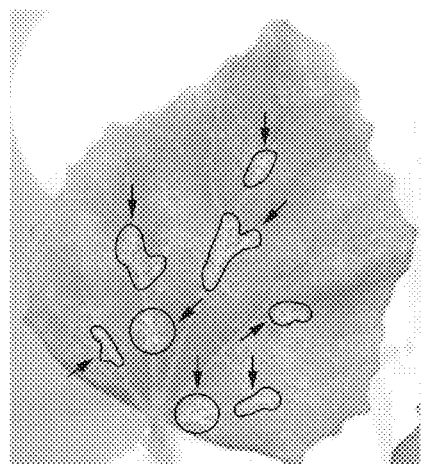
Figure 2D:
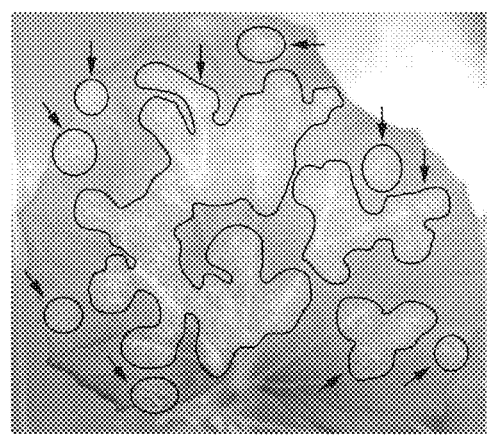

In the disease investigation, with reference to the method described in the above Reference Document 2, the disease index of the leaves of the melon plants subjected to the investigation was evaluated in accordance with the following criteria. FIGS. 2A to 2D show, as the evaluation criteria for the disease index, photographs showing representative examples of leaves of melon plants with a disease index 0 (FIG. 2A), a disease index 1 (FIG. 2B), a disease index 2 (FIG. 2C), and a disease index 3 (FIG. 2D). In these photographs, a region where sporulation is observed is outlined with a solid line and indicated with an arrow.

Disease index 0: Sporulation is not observed (highly resistant).
Disease index 1: Slight sporulation is observed (resistant).
Disease index 2: Sporulation is observed in a limited region.
Disease index 3: High level of sporulation is observed over a broad region.

The results obtained are shown in Table 1 below. As can be seen in Table 1, in the 61 lines, the number of the individuals exhibited a disease index of 1 or less, i.e., the individuals resistant to powdery mildew was 15, which accounted for 24.6% of the total number of the individuals. From the relationship between the disease indices of the 61 lines and the frequencies of appearance of the individuals having the corresponding disease indices, it was found that the mode of inheritance of the powdery mildew resistance of the deposited line was monogenic recessive. The susceptible melon plants subjected to the disease investigation under the same conditions were found to be susceptible to powdery mildew. Further, the deposited line was found to be resistant to powdery mildew. A monogenic recessive powdery mildew resistance locus had not been known. Therefore, it was found that the powdery mildew resistance locus included in the deposited line is a novel powdery mildew resistance locus.

TABLE 1

| | Disease index | | | | Total number of individuals | Proportion of individuals with disease index of 1 or less |
|---|---|---|---|---|---|---|
| | 0 | 1 | 2 | 3 | | |
| Deposited line | 7 | 3 | 0 | 0 | 10 | 100% |
| Susceptible melon plants | 0 | 0 | 2 | 8 | 10 | 0% |
| F2 segregating population | 9 | 6 | 8 | 38 | 10 | 24.6% |

(3) Identification of Novel Powdery Mildew Resistance Locus

Subsequently, DNA was extracted from each of the 61 lines by an ordinary method. Further, the DNA was subjected to DNA assay. Then, on the basis of the disease index determined in the above item (2) and the result of the DNA assay, QTL analysis was performed using analysis software (QTL cartographer, NC STATE University). As a result, on chromosome 6, one region with high correlation with the disease index was identified. The region with high correlation is a region including the base sequence that forms the amplified fragment when amplified using the primer set 1 and the first SNP set. From these results, it was found that the novel powdery mildew resistance locus includes a monogenic recessive gene on chromosome 6. Also, as a result of analysis of the base sequence of the region with high correlation, it was found that the powdery mildew resistant melon plants were each such that the lengths of amplified fragments amplified from two copies of chromosome 6 using the primer set 1 are both 133 bp; on the two copies of chromosome 6, $SNP1_{45}$, $SNP1_{48}$, $SNP1_{49}$, $SNP1_{51}$, $SNP1_{108}$, $SNP1_{120}$, $SNP1_{139}$, $SNP1_{214}$, and $SNP1_{327}$ are A, A, T, T, T, A, A, T and C, respectively; and the two copies of chromosome 6 each include the base sequence from positions 204 to 213 in the base sequence of SEQ ID NO: 3.

(4) Novel Powdery Mildew Resistance Locus and Powdery Mildew Resistance

The DNA of each of the 61 lines was amplified by PCR using the primer set 1, and the lengths of the amplified fragments obtained by the amplification were measured. Also, the DNA of each of the 61 lines was amplified by PCR using the following primer set 2, and polymorphic bases corresponding to the first SNP set were identified in the amplified fragments obtained by the amplification. The amplification using the primer set 1 was carried out by incubating the DNA at 94° C. for 3 minutes, then subjecting the DNA to 35 cycles of treatment (with a treatment at 94° C. for 30 seconds, at 57° C. for 30 seconds, and at 72° C. for 60 seconds as one cycle), and subsequently incubating the DNA at 72° C. for 3 minutes. The amplification using the primer set 2 was carried out by incubating the DNA at 94° C. for 3 minutes, then subjecting the DNA to 35 cycles of treatment (with a treatment at 94° C. for 30 seconds, at 56° C. for 30 seconds, and at 72° C. for 60 seconds as one cycle), and subsequently incubating the DNA at 72° C. for 3 minutes. Then, on the basis of the lengths of the amplified fragments and the polymorphic bases corresponding to the first SNP set, the 61 lines were classified into resistant-type homozygous melon plants (A), heterozygous melon plants (H), and susceptible-type homozygous melon plants (B). The results thereof are shown in Table 2 below. In Table 2 below, "A" indicates individuals for which it was found that the lengths of the amplified fragments obtained by amplification from the two copies of chromosome 6 were both 133 bp or more and the first SNP set was in the resistant-type homozygous form. "H" indicates individuals for which it was found that the length of the amplified fragment obtained by amplification from one of the two copies of chromosome 6 was 133 bp or more, the length of the amplified fragment obtained by amplification from the other copy of chromosome 6 was less than 133 bp and the first SNP set was in the heterozygous form. "B" indicates individuals for which it was found that the lengths of the amplified fragments obtained by amplification from the two copies of chromosome 6 were both less than 133 bp and the first SNP set was in the susceptible-type homozygous form.

```
Primer set 2
a forward primer 2:
                                        (SEQ ID NO: 8)
5'-GGAAAAATGCAGGGGAAG-3' a reverse primer 2:
                                        (SEQ ID NO: 9)
5'-CTGCCAAAAGCGACTTAACC-3'
```

TABLE 2

| Genotype | Disease index | | | | Total number of individuals | Proportion of individuals with disease index of 1 or less |
| --- | --- | --- | --- | --- | --- | --- |
| | 0 | 1 | 2 | 3 | | |
| A | 9 | 6 | 0 | 0 | 15 | 100% |
| H | 0 | 0 | 7 | 23 | 30 | 0% |
| B | 0 | 0 | 1 | 15 | 16 | 0% |

As can be seen in Table 2, the individuals classified as "A" all exhibited a disease index of 1 or less. On the other hand, the individuals classified as "H" and "B" all exhibited a disease index of 2 or more. These results demonstrate that the novel powdery mildew resistance locus identified by the lengths of the amplified fragments and the first SNP set is responsible for the powdery mildew resistance. Also, from the fact that the resistance locus identified by the lengths of the amplified fragments and the first SNP set, i.e., the resistance locus that satisfies both the conditions (1) and (2) is responsible for the powdery mildew resistance, it was found that the resistance locus serves as a powdery mildew resistance marker for melon plants and that screening for powdery mildew resistant melon plants is possible by using the powdery mildew resistance marker for melon plants.

(5) Examination of Resistance to Known Powdery Mildew Fungi

From the 61 lines, 10 lines of the resistant-type homozygous individuals were selected. Next, each of the 10 lines was self-crossed to produce an F3 selected line. Further, regarding the thus-produced ten F3 selected lines (F3-1 to F3-10), a powdery mildew fungus inoculation test was carried out in the same manner as in the above item (2) using 10 individuals for each F3 selected line. Then, the disease indices were determined for the respective F3 selected lines. The disease index of the corresponding F3 selected line was determined according to the following equation.

Disease index=$[(0×n_0)+(1×n_1)+(2×n_2)+(3×n_3)]$/the number of the investigated individuals In the above equation, "0, 1, 2, and 3" each indicate a disease index, and "no, $n_1$, $n_2$, and $n_3$" indicate the number of individuals evaluated as having a disease index of 0, a disease index of 1, a disease index of 2, and a disease index of 3, respectively.

In the powdery mildew fungus inoculation test, a powdery mildew fungus line 2 (race 2F), a powdery mildew fungus line 3 (race 5), and a powdery mildew fungus line 4 (race G) were used, in addition to the powdery mildew fungus line 1. Also, the powdery mildew fungus inoculation test was carried out and the disease index was evaluated in the same manner as in the above, except that, instead of the F3 selected lines, the following melon plants were used: as known powdery mildew susceptible melon plants, Vedrantais (available from the following website: http://www-.burpee.com/heirloom-seeds-and-plants/heirloom-melons/melon-vedrantais-prod002040.html), PMR45 (available from United States Department of Agriculture [USDA] as PI601383), and the above-described susceptible melon plants; as known powdery mildew resistant melon plants, PMR5 (available from USDA as Ames26809), WMR29 (available from Institut National de la Recherche Agronomique [INRA]), Edisto47 (available from USDA as NSL34600), PI414723 (available from USDA), MR1 (available from INRA), and PI124112 (available from USDA); and the deposited line. The races of the powdery mildew fungus were determined with reference to the above Reference Document 3. The results obtained are shown in Table 3.

TABLE 3

|  | Line 1 (Race 3.5) | Line 2 (Race 2F) | Line 3 (Race 5) | Line 4 (Race G) |
|---|---|---|---|---|
| Vedrantais | 3 | 3 | 3 | 3 |
| PMR45 | 3 | 3 | 3 | 3 |
| PMR5 | 3 | 0 | 0 | 3 |
| WMR29 | 3 | 0 | 3 | 3 |
| Edisto47 | 3 | 0 | 3 | 3 |
| PI414723 | 0 | 0 | 0 | 3 |
| MR1 | 3 | 0 | 0 | 0 |
| PI124112 | 3 | 0 | 0 | 3 |
| Susceptible melon plants | 3 | 3 | 3 | 3 |
| Deposited line | 0.3 | 0.2 | 0.1 | 0.1 |
| F3-1 | 0.2 | 0.3 | 0.2 | 0.1 |
| F3-2 | 0.1 | 0.2 | 0.2 | 0.2 |
| F3-3 | 0.1 | 0.1 | 0.3 | 0.2 |
| F3-4 | 0.2 | 0.1 | 0.1 | 0.1 |
| F3-5 | 0.1 | 0.2 | 0.3 | 0.2 |
| F3-6 | 0.1 | 0.3 | 0.1 | 0.1 |
| F3-7 | 0.2 | 0.1 | 0.2 | 0.2 |
| F3-8 | 0.2 | 0.2 | 0.1 | 0.3 |
| F3-9 | 0.3 | 0.2 | 0.1 | 0.1 |
| F3-10 | 0.1 | 0.1 | 0.2 | 0.1 |

As can be seen in Table 3, the known powdery mildew susceptible melon plants Vedrantais and PMR45 and the above-described susceptible melon plants were all susceptible to all the powdery mildew fungus lines. The known powdery mildew resistant melon plants PMR5 and PI124112 were resistant to the powdery mildew fungus lines 2 and 3, whereas they were susceptible to the powdery mildew fungus lines 1 and 4. WMR29 and Edisto47 were resistant to the powdery mildew fungus line 2, whereas they were susceptible to the powdery mildew fungus lines 1, 3, and 4. PI414723 was resistant to the powdery mildew fungus lines 1 to 3, whereas it was susceptible to the powdery mildew fungus line 4. MR1 was resistant to the powdery mildew fungus lines 2 to 4, whereas it was susceptible to the powdery mildew fungus line 1. In contrast, the F3 selected lines and the deposited line were resistant to all the powdery mildew fungus lines. Further, since the powdery mildew fungus lines 1 to 4 are all capable of infecting melon plants including known powdery mildew resistance genes, it was found that the resistance locus also is effective against the powdery mildew fungus lines capable of infecting melon plants including known powdery mildew resistance genes. These results demonstrate that the F3 selected lines and the deposited line are resistant to a plurality of known races of powdery mildew fungi. Moreover, while the known powdery mildew resistant melon plants were susceptible to at least one of the powdery mildew fungus lines 1 to 4, the F3 selected lines and the deposited line were resistant to all the powdery mildew fungus lines 1 to 4. These results demonstrate that the resistance locus that satisfies both the conditions (1) and (2) is a novel powdery mildew resistance locus different from resistance loci included in known powdery mildew resistant melon plants.

(6) Powdery Mildew Resistance Locus on Chromosome 6

An F2 segregating population was produced in the same manner as in the above item (2). Then, regarding the thus-produced F2 segregating population, the lengths of the amplified fragments and polymorphic bases corresponding to the first SNP set were identified in the same manner as the above item (4). Further, DNA of each individual of the F2 segregating population was amplified by PCR using the following primer sets 3 and 4, and polymorphic bases corresponding to the second SNP set and the third SNP set in the amplified fragments obtained by the amplification were identified. The amplification using the primer set 3 was carried out by incubating the DNA at 94° C. for 3 minutes, then subjecting the DNA to 35 cycles of treatment (with a treatment at 94° C. for 30 seconds, at 51° C. for 30 seconds, and at 72° C. for 60 seconds as one cycle), and subsequently incubating the DNA at 72° C. for 3 minutes. The amplification using the primer set 4 was carried out by incubating the DNA at 94° C. for 3 minutes, then subjecting the DNA to 35 cycles of treatment (with a treatment at 94° C. for 30 seconds, at 58° C. for 30 seconds, and at 72° C. for 60 seconds as one cycle), and subsequently incubating the DNA at 72° C. for 3 minutes.

```
Primer set 3
a forward primer 3:
                                (SEQ ID NO: 10)
5'-AGGAAACGAAGAATAGACG-3' a reverse primer 3:
                                (SEQ ID NO: 11)
5'-TGAGAACCGGAAAGAGAAGC-3'

Primer set 4
a forward primer 4:
                                (SEQ ID NO: 12)
5'-GTTCGGATCGGAAAATTCAA-3' a reverse primer 4:
                                (SEQ ID NO: 13)
5'-CCAAGCTTTCCGACATTCAT-3'
```

Then, regarding the F2 segregating population, the lengths of the amplified fragments and the genotypes of the first SNP set, the second SNP set, and the third SNP set were classified. Also, regarding the F2 segregating population, the powdery mildew fungus inoculation test was carried out and the disease index was evaluated in the same manner as in the above item (2). Among the results obtained, Table 4 shows the results obtained regarding four individuals (lines X1 to X4) that differ from one another in the lengths of the amplified fragments and the genotypes of the first SNP set, the second SNP set, and the third SNP set; the deposited line; the susceptible line; and F1 lines obtained from the deposited line and the susceptible line. Regarding the lengths of the amplified fragments shown in Table 4 below, "A" indicates that the lengths of the amplified fragments obtained by amplification from the two copies of chromosome 6 using the primer set 1 were both 133 bp or more. "H" indicates that the length of the amplified fragment obtained by amplification from one of two copies of chromosome 6 using the primer set 1 was 133 bp or more, and the length of the amplified fragment obtained by amplification from the other copy of chromosome 6 was less than 133 bp. "B" indicates that the lengths of the amplified fragments obtained by amplification from the two copies of chromosome 6 were both less than 133 bp. Further, regarding the first SNP set, the second SNP set, and the third SNP set shown in Table 4 below, "A" indicates that each of the SNP sets was in the resistant-type homozygous form, "H" indicates that each of the SNP sets was in the heterozygous form, and "H" indicates that each of the SNP sets was in the susceptible-type homozygous form. In Table 4, A is shaded.

TABLE 4

| | Second SNP set | Lengths of amplification fragments | First SNP set | Third SNP set | Disease index |
|---|---|---|---|---|---|
| Line X1 | H | A | A | A | 0 |
| Line X2 | A | H | H | H | 3 |
| Line X3 | H | H | H | A | 3 |
| Line X4 | H | A | A | H | 1 |
| Deposited line | A | A | A | A | 0 |
| F1 lines | H | H | H | H | 3 |
| Susceptible melon plant | B | B | B | B | 3 |

As can be seen in Table 4, all the individuals classified as "A" regarding the lengths of the amplified fragments and the first SNP set exhibited a disease index of 1 or less. From these results, it was found that, in the resistance locus, the lengths of the amplified fragments and the first SNP set show high correlation with the powdery mildew resistance. In other words, it was found that the conditions (1) and (2) show high correlation with the powdery mildew resistance. Also, from the fact that the lengths of the amplified fragments and the first SNP set show high correlation with the powdery mildew resistance, it was found that a region between the sites of any two SNPs selected from the second SNP set and the third SNP set, i.e., a region including the amplified fragments and the first SNP set, shows high correlation with the powdery mildew resistance. In other words, it was found that the condition (9) shows high correlation with the powdery mildew resistance. From these results, it was found that the resistance locus that satisfies at least one of the conditions (1) and (2) and the resistance locus that satisfies the condition (9) each serve as a powdery mildew resistance marker for melon plants and that screening for powdery mildew resistant melon plants is possible by using the powdery mildew resistance marker for melon plants.

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2015-222794 filed on Nov. 13, 2015. The entire disclosure of this Japanese patent application is incorporated herein by reference.

INDUSTRIAL APPLICABILITY

The powdery mildew resistance marker for melon plants according to the present invention enables easy screening for powdery mildew resistant melon plants, for example. Also, the powdery mildew resistant melon plant according to the present invention includes the powdery mildew resistance locus, for example, and thus can exhibit powdery mildew resistance, for example. Further, the powdery mildew resistance locus can confer the powdery mildew resistance while it is a single gene locus, for example. Thus, according to the powdery mildew resistant melon plant of the present invention, for example, progenies exhibiting powdery mildew resistance can be obtained easily also from F1 obtained by crossing the powdery mildew resistant melon plant of the present invention with other melon plants or progenies thereof. Furthermore, a melon plant including the powdery mildew resistance marker is resistant to races of powdery mildew fungus capable of infecting melon plants including the powdery mildew resistance genes disclosed in the prior art document, for example. Thus, the powdery mildew resistant melon plant of the present invention can eliminate the necessity of prevention and extermination using agricultural chemicals as performed conventionally, so that the problem of labor and cost for spraying the agricultural chemicals can be avoided, for example.

SEQUENCE LISTING

TF15023WO_ST25.txt

The invention claimed is:

1. A method for producing a melon plant, the method comprising the following step (x) and (a):
- (x) selecting a melon plant comprising a powdery mildew resistance locus on chromosome 6 in a homozygous form from one or more melon plants to be examined; and
- (a) crossing the melon plant comprising the powdery mildew resistance locus on chromosome 6 in a homozygous form with another cultivated melon plant; wherein the powdery mildew resistance locus on chromosome 6 satisfies at least one of the following conditions (1) and (2):
- Condition (1): the powdery mildew resistance locus on chromosome 6 is identified by a length of an amplified fragment obtained by amplification using primer set 1 comprising a forward primer 1 consisting of the sequence of SEQ ID NO: 1 and a reverse primer 1 consisting of the sequence of SEQ ID NO: 2, and the length of the amplified fragment is 133 bp or more, and
- Condition (2): the powdery mildew resistance locus on chromosome 6 is identified by polymorphisms of bases at positions 45, 48, 49, 51, 108, 120, 139, 214, and 327 in the sequence of SEQ ID NO: 3, wherein the bases at positions 45, 48, 49, 51, 108, 120, 139, 214, and 327 are A, A, T, T, T, A, A, T, and C, respectively.

2. The production method according to claim 1, wherein, in the condition (2), the powdery mildew resistance locus on chromosome 6 having said polymorphisms comprises AAAAGCTCCA at positions corresponding to positions 204 to 213 in the sequence of SEQ ID NO: 3.

3. The production method according to claim 1, wherein the powdery mildew resistance locus on chromosome 6 satisfies at least one of the following conditions (3) and (4):
- Condition (3): the powdery mildew resistance locus on chromosome 6 is identified by polymorphisms of bases at positions 50, 141, and 266 in the sequence of SEQ ID NO: 4, and
- Condition (4): the powdery mildew resistance locus on chromosome 6 is identified by polymorphisms of bases at positions 99, 174, 184, 199, and 200 in the sequence of SEQ ID NO: 5.

4. The production method according to claim 1, wherein the powdery mildew resistance locus on chromosome 6 satisfies at least one of the following conditions (5) and (6):
- Condition (5): the powdery mildew resistance locus on chromosome 6 is identified by (a1) a polynucleotide consisting of the sequence of SEQ ID NO: 6, or (a3) a polynucleotide consisting of a sequence having at least 90% sequence identity to the sequence of the polynucleotide (a1),
- Condition (6): the powdery mildew resistance locus on chromosome 6 is identified by (b1) a polynucleotide consisting of the sequence of SEQ ID NO: 3, or (b3) a polynucleotide consisting of a sequence having at least 90% sequence identity to the sequence of the polynucleotide (b1) in which the base (A) at position 45, the base (A) at position 48, the base (T) at position 49, the base (T) at position 51, the base (T) at position 108, the base (A) at position 120, the base (A) at position 139, the base (T) at position 214, and the base (C) at position 327 in the sequence of the polynucleotide (b1) are conserved.

5. The production method according to claim 1, wherein the powdery mildew resistance locus on chromosome 6 satisfies at least one of the following conditions (7) and (8):
- Condition (7): the powdery mildew resistance locus on chromosome 6 is identified by (c1) a polynucleotide consisting of the sequence of SEQ ID NO: 4, or (c3) a polynucleotide consisting of a sequence having at least 80% sequence identity to the sequence of the polynucleotide (c1) in which the base (C) at position 50, the base (A) at position 141, and the base (T) at position 266 in the sequence of the polynucleotide (c1) are conserved,
- Condition (8): the powdery mildew resistance locus on chromosome 6 is identified by (d1) a polynucleotide consisting of the sequence of SEQ ID NO: 5, or (d3) a polynucleotide consisting of a sequence having at least 80% sequence identity to the sequence of the polynucleotide (d1) in which the base (C) at position 99, the base (G) at position 174, the base (T) at position 184, the base (A) at position 199, and the base (T) at position 200 in the sequence of the polynucleotide (d1) are conserved.

6. A method for producing a melon plant, the method comprising the following step (a) and (b):
- (a) crossing a melon plant comprising a powdery mildew resistance locus on chromosome 6 in a homozygous form with another cultivated melon plant; and
- (b) selecting a powdery mildew resistant melon plant comprising the powdery mildew resistance locus on chromosome 6 in a homozygous form from one or more melon plants obtained from the step (a) or progeny lines thereof; wherein the powdery mildew resistance locus on chromosome 6 satisfies at least one of the following conditions (1) and (2):
- Condition (1): the powdery mildew resistance locus on chromosome 6 is identified by a length of an amplified fragment obtained by amplification using primer set 1 comprising a forward primer 1 consisting of the sequence of SEQ ID NO: 1 and a reverse primer 1 consisting of the sequence of SEQ ID NO: 2, and the length of the amplified fragment is 133 bp or more, and Condition (2): the powdery mildew resistance locus on chromosome 6 is identified by polymorphisms of bases at positions 45, 48, 49, 51, 108, 120, 139, 214, and 327 in the sequence of SEQ ID NO: 3, wherein the bases at positions 45, 48, 49, 51, 108, 120, 139, 214, and 327 are A, A, T, T, T, A, A, T, and C, respectively.

7. The production method according to claim 6, wherein, in the condition (2), the powdery mildew resistance locus on chromosome 6 having said polymorphisms comprises AAAAGCTCCA at positions corresponding to positions 204 to 213 in the sequence of SEQ ID NO: 3.

8. The production method according to claim 6, wherein the powdery mildew resistance locus on chromosome 6 satisfies at least one of the following conditions (3) and (4):

Condition (3): the powdery mildew resistance locus on chromosome 6 is identified by polymorphisms of bases at positions 50, 141, and 266 in the sequence of SEQ ID NO: 4, and Condition (4): the powdery mildew resistance locus on chromosome 6 is identified by polymorphisms of bases at positions 99, 174, 184, 199, and 200 in the sequence of SEQ ID NO: 5.

9. The production method according to claim 6, wherein the powdery mildew resistance locus on chromosome 6 satisfies at least one of the following conditions (5) and (6):

Condition (5): the powdery mildew resistance locus on chromosome 6 is identified by (a1) a polynucleotide consisting of the sequence of SEQ ID NO: 6, or (a3) a polynucleotide consisting of a sequence having at least 90% sequence identity to the sequence of the polynucleotide (a1), Condition (6): the powdery mildew resistance locus on chromosome 6 is identified by (b1) a polynucleotide consisting of the sequence of SEQ ID NO: 3, or (b3) a polynucleotide consisting of a sequence having at least 90% sequence identity to the sequence of the polynucleotide (b1) in which the base (A) at position 45, the base (A) at position 48, the base (T) at position 49, the base (T) at position 51, the base (T) at position 108, the base (A) at position 120, the base (A) at position 139, the base (T) at position 214, and the base (C) at position 327 in the sequence of the polynucleotide (b1) are conserved.

10. The production method according to claim 6, wherein the powdery mildew resistance locus on chromosome 6 satisfies at least one of the following conditions (7) and (8):

Condition (7): the powdery mildew resistance locus on chromosome 6 is identified by (c1) a polynucleotide consisting of the sequence of SEQ ID NO: 4, or (c3) a polynucleotide consisting of a sequence having at least 80% sequence identity to the sequence of the polynucleotide (c1) with the base (C) at position 50, the base (A) at position 141, and the base (T) at position 266 in the sequence of the polynucleotide (c1) being conserved, and Condition (8): the powdery mildew resistance locus on chromosome 6 is identified by (d1) a polynucleotide consisting of the sequence of SEQ ID NO: 5, or (d3) a polynucleotide consisting of a sequence having at least 80% sequence identity to the sequence of the polynucleotide (d1) in which the base (C) at position 99, the base (G) at position 174, the base (T) at position 184, the base (A) at position 199, and the base (T) at position 200 in the sequence of the polynucleotide (d1) are conserved, wherein the powdery mildew resistant melon plant is a melon plant deposited with the International Patent Organism Depositary National Institute of Technology and Evaluation under Accession No. FERM BP-22291 or a progeny line thereof.

11. A method for producing a powdery mildew resistant melon plant, the method comprising the following step (a):

(a) crossing a melon plant comprising a powdery mildew resistance locus on chromosome 6 in a homozygous form with another cultivated melon plant; wherein the powdery mildew resistance locus on chromosome 6 satisfies at least one of the following conditions (1) and (2):

Condition (1): the powdery mildew resistance locus on chromosome 6 is identified by a length of an amplified fragment obtained by amplification using primer set 1 comprising a forward primer 1 consisting of the sequence of SEQ ID NO: 1 and a reverse primer 1 consisting of the sequence of SEQ ID NO: 2, and the length of the amplified fragment is 133 bp or more, and Condition (2): the powdery mildew resistance locus on chromosome 6 is identified by polymorphisms of bases at positions 45, 48, 49, 51, 108, 120, 139, 214, and 327 in the sequence of SEQ ID NO: 3 wherein the powdery mildew resistant melon plant is a melon plant deposited with the International Patent Organism Depositary National Institute of Technology and Evaluation under Accession No. FERM BP-22291 or a progeny line thereof.

* * * * *